(12) United States Patent
Sahadevan

(10) Patent No.: US 7,902,530 B1
(45) Date of Patent: Mar. 8, 2011

(54) MULTIPLE MEDICAL ACCELERATORS AND A KV-CT INCORPORATED RADIATION THERAPY DEVICE AND SEMI-AUTOMATED CUSTOM RESHAPEABLE BLOCKS FOR ALL FIELD SYNCHRONOUS IMAGE GUIDED 3-D-CONFORMAL-INTENSITY MODULATED RADIATION THERAPY

(76) Inventor: Velayudhan Sahadevan, Beckley, WV (US)

( * ) Notice: Subject to any disclaimer, the term of this patent is extended or adjusted under 35 U.S.C. 154(b) by 64 days.

(21) Appl. No.: 11/974,876

(22) Filed: Oct. 15, 2007

Related U.S. Application Data

(63) Continuation of application No. 11/784,398, filed on Apr. 5, 2007, now abandoned.

(60) Provisional application No. 60/790,192, filed on Apr. 6, 2006.

(51) Int. Cl.
*A61N 5/10* (2006.01)

(52) U.S. Cl. ............. 250/494.1; 250/492.1; 250/492.3; 250/341.7; 378/64; 378/65; 600/427; 600/9

(58) Field of Classification Search .......... 250/492.1, 250/493.1, 496.1, 505.1, 336.1, 339.06, 340, 250/341.7, 362, 363.01, 363.02, 370.08, 250/370.09, 492.3, 494.1; 378/64, 65, 101, 378/108, 119, 145, 137, 138, 901; 600/427, 600/9, 10; 128/897, 920

See application file for complete search history.

(56) References Cited

U.S. PATENT DOCUMENTS

| | | | | |
|---|---|---|---|---|
| 4,723,750 A | * | 2/1988 | Clark, III | 249/111 |
| 4,827,491 A | * | 5/1989 | Barish | 378/65 |
| 4,868,843 A | * | 9/1989 | Nunan | 378/152 |
| 4,938,277 A | * | 7/1990 | Korver | 164/137 |
| 5,596,619 A | | 1/1997 | Carol | |
| 5,802,136 A | * | 9/1998 | Carol | 378/65 |
| 5,842,987 A | * | 12/1998 | Sahadevan | 600/407 |
| 5,851,182 A | * | 12/1998 | Sahadevan | 600/407 |
| 5,866,914 A | * | 2/1999 | Jones | 250/505.1 |
| 6,080,992 A | * | 6/2000 | Nonaka et al. | 250/505.1 |
| 6,381,304 B1 | * | 4/2002 | Shoenfeld et al. | 378/65 |
| 6,576,915 B1 | * | 6/2003 | McIntyre | 250/492.3 |
| 6,735,277 B2 | * | 5/2004 | McNutt et al. | 378/65 |
| 2003/0086527 A1 | * | 5/2003 | Speiser et al. | 378/65 |
| 2003/0123609 A1 | * | 7/2003 | Manske | 378/65 |
| 2005/0058245 A1 | * | 3/2005 | Ein-Gal | 378/65 |
| 2005/0087703 A1 | * | 4/2005 | Merlo | 250/505.1 |

(Continued)

OTHER PUBLICATIONS

Hall, E.J. and Wuu, C. S. Radiation Induced Second Cancers: the Impact of 3-DCRT and IMRT, Int. J. Radiation Oncology, Biol. Phys., 56, p. 83-88, 2003.

(Continued)

*Primary Examiner* — Bernard E Souw
*Assistant Examiner* — Michael J Logie

(57) ABSTRACT

S-band, C-band or X-band microwave powered linear accelerators capable of delivering therapeutic photon and electron beams are mounted to a gantry with extensions to hold multiple accelerators and are combined with a kV CT for 3-D conformal—IMRT and IGRT to treat a patient by SSD or SAD methods and in a full circle. The invention's tertiary collimator system consists of semi-automated reusable custom field shaping with tungsten powder or melted Cerrobend blocks. The beam's intensity modulation is by means of simultaneous but independently operating multiple accelerators. This system's multiple accelerators enable to avoid interrupted subfractionated radiation therapy to each treatment fields. Hence its effective dose rate at the tumor site is high. The improved radiobiology reduces the total radiation dose to treat a tumor, reducing the incidence of developing second primary tumors is also minimized.

15 Claims, 17 Drawing Sheets

U.S. PATENT DOCUMENTS

| | | | | |
|---|---|---|---|---|
| 2006/0255285 | A1* | 11/2006 | Jongen et al. | 250/396 ML |
| 2007/0040127 | A1* | 2/2007 | Brahme et al. | 250/389 |
| 2007/0041500 | A1* | 2/2007 | Olivera et al. | 378/65 |
| 2007/0221869 | A1* | 9/2007 | Song | 250/492.1 |
| 2008/0049892 | A1* | 2/2008 | Maltz | 378/19 |
| 2008/0064953 | A1* | 3/2008 | Falco et al. | 600/427 |

OTHER PUBLICATIONS

Smith M.A., Rubenstein L., Anderson, J.R., Secondary Leukaemia or myloplastic Syndrome after Treatment with epipodophyllotoxins, J. Clin Oncol. 17, p. 569, 1999.

Xu T. et al, Reshapeable Physical Modulator for IMRT, Am. Assoc. Phys. Med. vol. 29, No. 10, Oct. 2002, p. 2222-2229.

Khan, F.M., Tomotherapy, p. 488-491, in Chapter 20, Intensity Modulated Radiation Therapy, p. 481-506 : The Physics of Radiation Therapy, Khan F.M.(ed), 2003, Lippencott.

Xia P. et al., Inverse Planning, p. 167-169, in Text book of Radiation Oncology; ed. Steven A. Liebel and Theodore L. Phillips, 2004, Saunders.

Hall, E.J., Direct and indirect Action of Radiation, p. 12-14 in Radiobiology for the Radiologist, Fifth Edition, 2000, Lippencott & Wilkins, Philadelphia.

Hall, E.J., Shape of the Survival Curve, p. 35-37, in Radiobiology for the Radiologist, Fifth Edition, 2000, Lippencott & Wilkins, Philadelphia.

Hall, E.J., Sublethal Damage Repair, p. 68-72, in Radiobiology for the Radiologist, Fifth Edition, 2000, Lippencott & Wilkins, Philadelphia.

Hall, E.J., The Strandquist Plot and Ellis Nominal Standard Dose System, p. 398-399, in Radiobiology for the Radiologist, Fifth Edition, 2000, Lippencott & Wilkins, Philadelp.

Xia P. et.al., More on Static versus Dynamic Multileaf Collimator Delivery, p. 177-178, In Textbook of Radiation Oncology, Leibel & Phillips ed. 2nd Eddition, 2004, Saunders, P.

Hall, E.J., Biologic Basis of Chemotherapy, p. 471, in Radiobiology for the Radiologist, Fifth Edition, 2000, Lippencott & Wilkins, Philadelphia.

Xia P. et. al., Characteristics of MLCs, p. 174-177, in Text book of Radiation Oncology; Leibel & Phillips ed. 2nd Eddition, 2004, Saunders, Philadelphia.

Khan, F.M., Field Shaping, Custom Blocking p. 274-275, The Physics of Radiation Therpay, 3rd Edition, 2003, Lippencott, Williams & Wilkins, Philadelphia.

Ping Xia et al, Delivery of Intensity-Modulated Treatment, p. 172-174, In Textbook of Radiation Oncology, Leibel & Phillips ed. 2nd Eddition, 2004, Saunders, Philadelphia.

Khan, F.M., Multisegmented Static Fields Delivery, p. 484-485, The Physics of Radiation Therapy: 3rd Edition, 2003, Lippencott, Williams & Wilkins, Philadelphia.

Xia P. et al., Delineation of Treatment Volume and Critical Organs,p. 166, in Text book of Radiation Oncology; Leibel & Phillips ed. 2nd Eddition, 2004, Saunders, Philadelphia.

Khan, F.M., Imaging Data, p. 469-471, in Chapter 19, Three Dimensional Conformal Radiation Therapy, p. 467-480: The Physics of Radiation Therapy, Khan F.M.(ed), 2003, Lippencot.

Xia P.et. al, 3DCRT and IMRT Treatment Planning Process, p. 163-165, In Textbook of Radiation Oncology, Leibel & Phillips ed. 2nd Eddition, 2004, Saunders, Philadelphia.

C. Lu et al, Flowing Tungston Powder for Possible Use as the Primary Target at a Mueon Collider Source, Princeton/μμ/98-10, Mar. 15, 1998.

\* cited by examiner

FIGURE 3-A
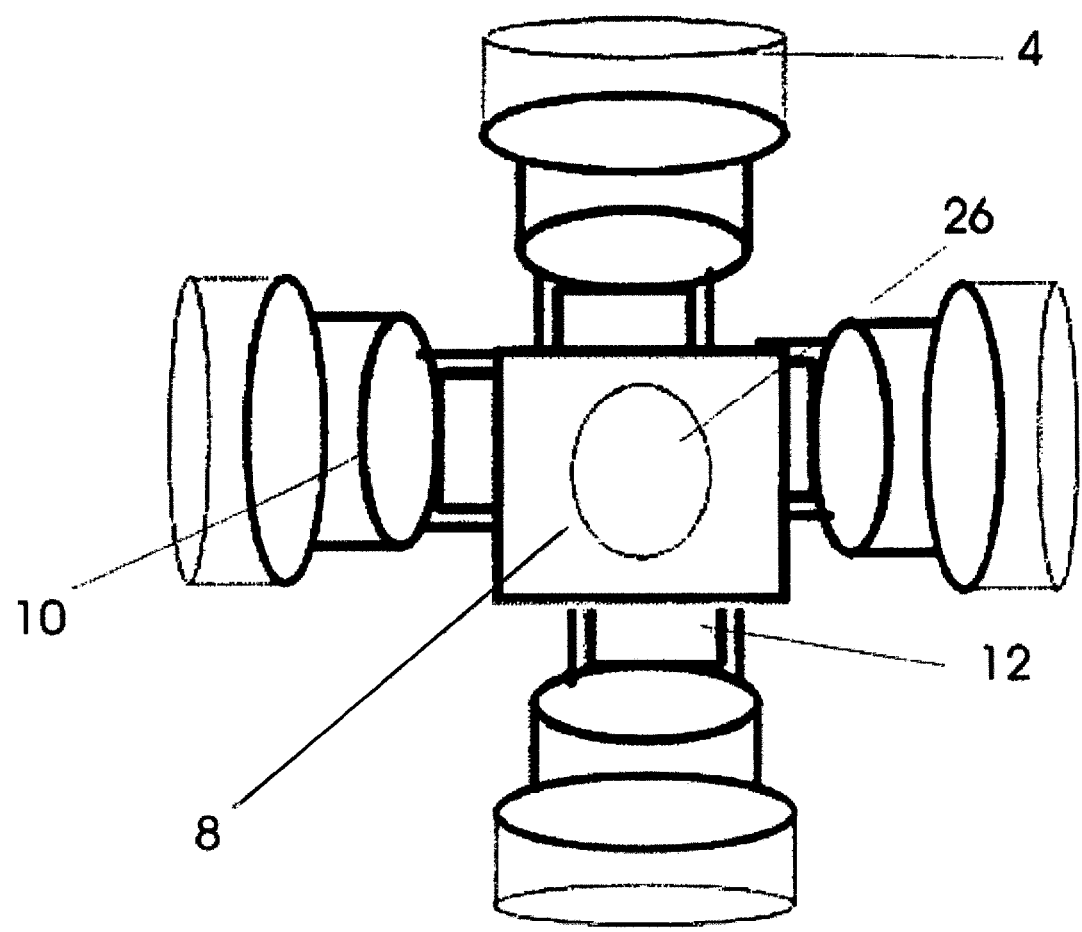

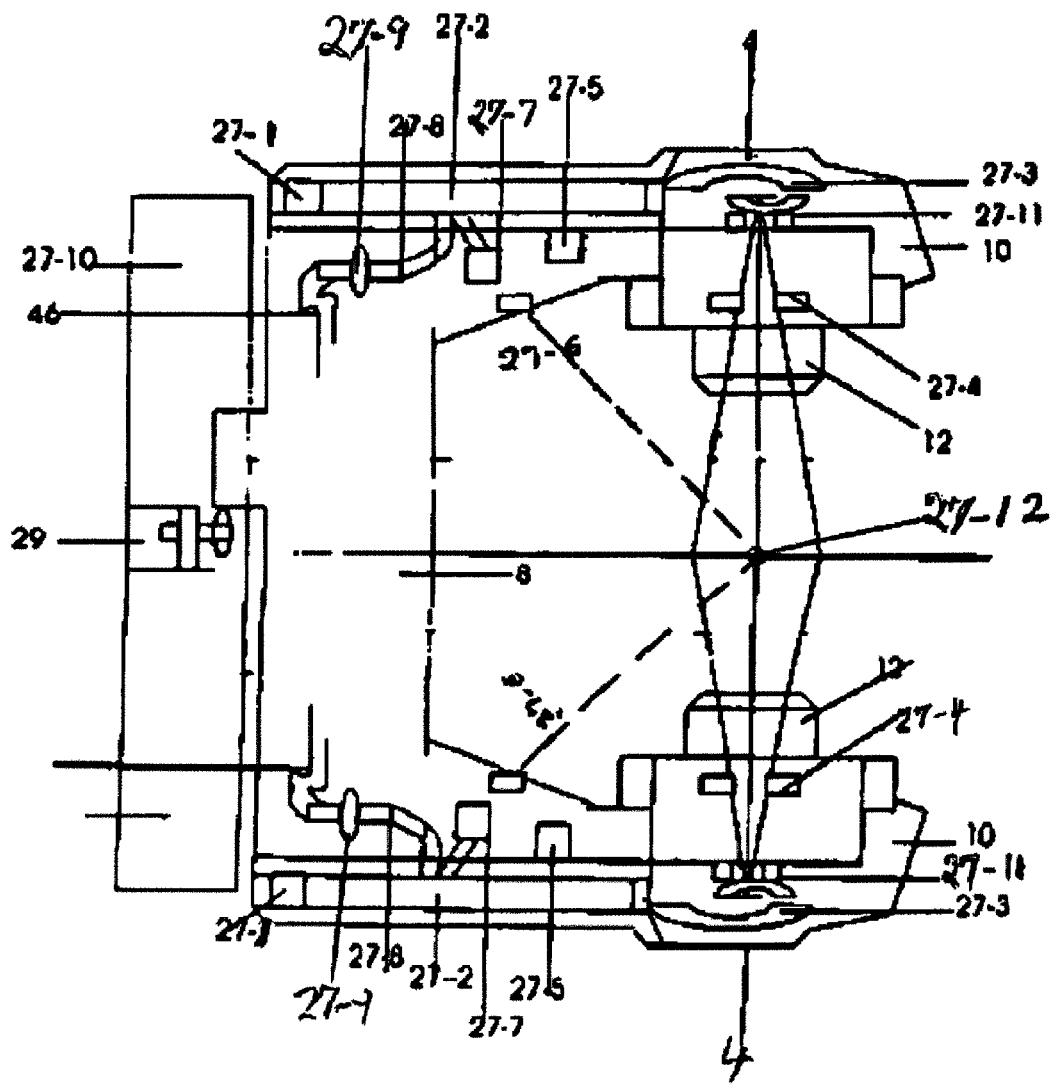
FIGURE 3-B-1
AT 0 AND 180 DEGREES

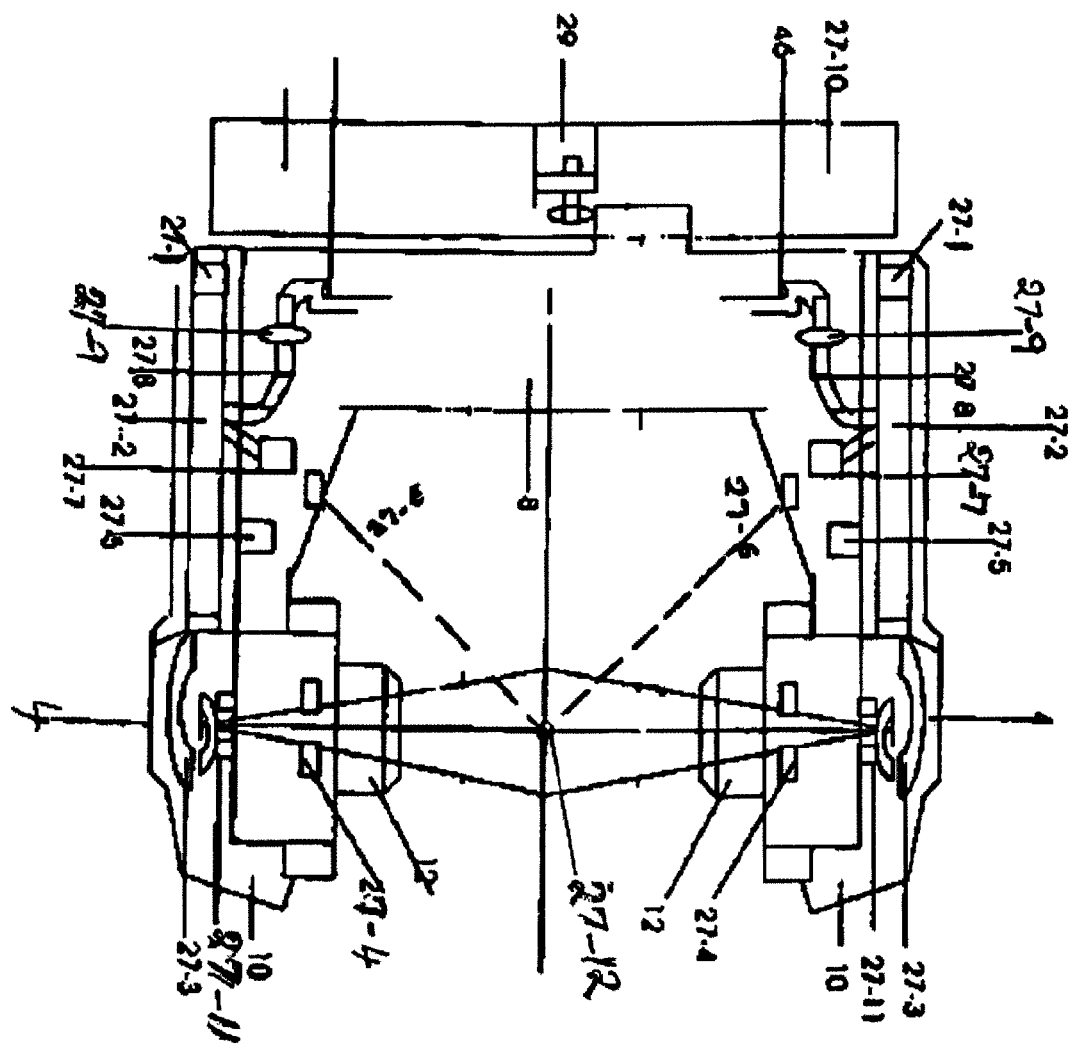
FIGURE 3-B-2
AT 90 AND 270 DEGREES

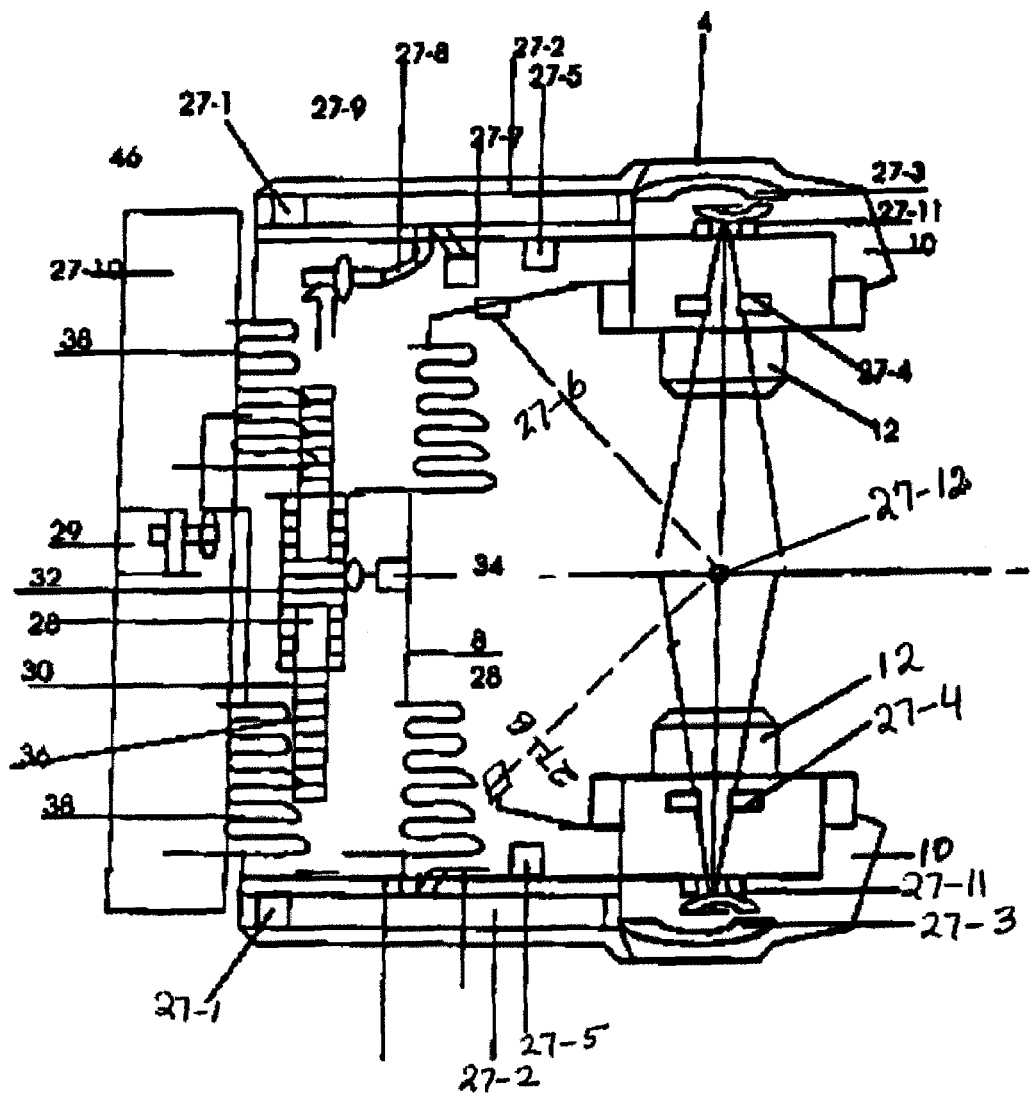
FIGURE 3-C-1
AT 0 AND 180 DEGREES

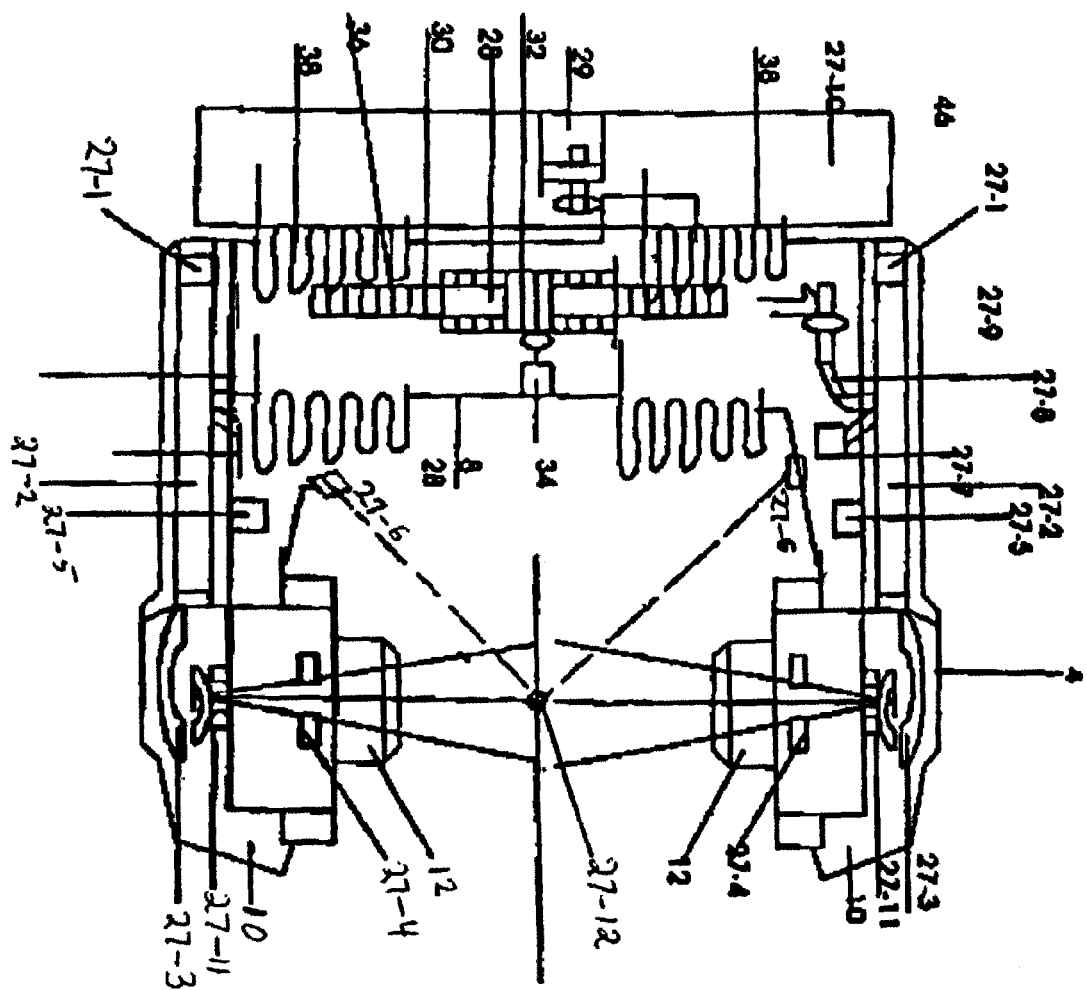
FIGURE 3-C-2
AT 90 AND 270 DEGREES

MULTIPLE MEDICAL ACCELERATORS AND A KV-CT INCORPORATED RADIATION THERAPY DEVICE AND SEMI-AUTOMATED CUSTOM RESHAPEABLE BLOCKS FOR ALL FIELD SYNCHRONOUS IMAGE GUIDED 3-D-CONFORMAL-INTENSITY MODULATED RADIATION THERAPY

CROSS REFERENCE TO RELATED APPLICATIONS

This is a continuation of U.S. patent application Ser. No. 11/784,398, filed on Apr. 5, 2007 now abandoned, and claims the benefit of U.S. Provisional Patent Application No. 60/790, 192 filed on Apr. 6, 2006.

FIELD OF INVENTION

This invention relates to multiple medical accelerators mounted on to a gantry for simultaneous radiation therapy to all treatment fields to improve tumor cure and control while minimizing lower dose radiation to normal tissue.

BACKGROUND OF THE INVENTION

To minimize immediate and late toxic effects of radiation to normal tissue, most often radiation is administered through multiple treatment fields. Smaller fractions of daily prescribed dose of radiation are given to each of the treatment fields. The radiation from such multiple fields converges at the tumor site to give the daily fractionated dose of radiation. The sum of the radiation dose from each of such smaller fields makes the prescribed daily dose of radiation to the tumor.

Radiating a tumor by multiple fields with a single accelerator is an interrupted daily fractionated radiation of the tumor. After setting up a patient in treatment position on the treatment table to treat the first field and after its various checks and verifications and treating, the gantry with the treatment head has to be rotated to bring it to the next treatment field. It follows a number of checks and verifications for the accuracy of this second treatment field's set up before its treatment and subsequent treatment. If it were a four fields daily fractionated radiation therapy, then this process of rotating the gantry with the treatment head from one position to the other to bring the radiation beam from each of those fields directed towards the tumor and checking and verification for the accuracy of each field's set up before radiating is repeated four times. If it were a six or eight field daily fractionated radiation therapy set up, then this process of field set up on the patient for radiation and checking for its accuracy before each field's radiation is repeated six or eight times respectively. After treating one field, the accelerator room with the patient positioned on the treatment table is opened to enter the room, to check the patient's condition, to rotate the gantry with the treatment head, to check the field set up and if the patient has moved then to readjust the treatment field set up and all other parameters of treatment before delivery of radiation to each fields. The patient setup has to be in conformity with the treatment planning. In some instances these process can take just a few minutes as in the case of a small segmented arc treatment. Most often it takes several minutes to deliver the daily prescribed dose to the tumor through multiple fields. Hence the present daily fractionated radiation therapy is a daily subfractionated radiation therapy that lasts from a few minutes to much longer periods.

There are computer controlled patient set up and treatment methods that could reduce the time required for the delivery of daily fractionated radiation therapy; still it is a lengthy interrupted, subfractionated daily radiation therapy. Moreover, all the treatment plans that look as good in the computer color screen may not be as good and accurate on the patient. The patients do move, especially when they are very sick and hence the need for verifications of each fields set up on the patient before delivery of radiation to a field of treatment.

As an example, it takes about 10 minutes to complete a computer controlled patient setup and treatment of a 6 segmented prostate cancer 3-D conformal radiation therapy; 6 minutes for the patient set up and 4 minutes for the treatment. The corresponding time to treat the prostate with blocks is 16 minutes. A six field's treatment by the present advanced segmental treatment delivering 180 to 200 cGy is equivalent to 30-33 cGy if these segments are not intensity modulated. Since this total dose of 180-200 cGy is delivered from multiple fields with lapsed time for setup and activation of the accelerator and delivery of radiation, it is in effect a subfractionated radiation therapy within the conventional daily 180-200 cGy fractionated radiation therapy.

It is also the case for different forms of intensity modulated radiation therapy (IMRT). The IMRT by multisegmented static fields, by dynamic IMRT, intensity modulated arch therapy all are subfractionated daily radiation therapy. Even the daily slice per slice treatment of a say 10×10 cm filed with the tomotherapy is a subfractionated radiation therapy. Based upon the slice thickness ranging from 0.5 to 5 cm that is used to complete daily radiation by tomotherapy, the time to complete the treatment is about 5 to 10 minutes. Hence the daily conventional and the 3-D conformal radiation therapy, the IMRT and the tomotherapy all are daily subfractionated radiation therapy within the daily-fractionated radiation therapy. Radiobiologically, its tumor cell kill is poor since it is dominated by $alphaD_1$. It is an inefficient method of radiation therapy.

In photon and electron beam radiation therapy, the indirect action of radiation on DNA predominates. The free hydroxyl radical (OH.) reacts with DNA to produce the DNA damage. The lifetime of the OH radicals outside the cell is $10^{-10}$ seconds and inside the cell; it is $10^{-9}$ seconds. The DNA radicals formed by the direct (high LET) or indirect action (OH.) have a lifetime of $10^{-5}$ seconds. Although the effects of such ionization of the cells may last for hours, days or years depending on the consequences involved, it is only a relative long term effect than those associated with the immediate cell kill effects from free OH radicals produced by radiation.

On the other hand if 180-200 cGy daily fractionated radiation is delivered to the tumor by radiating all the treatment fields simultaneously, all filed synchronous radiation therapy (AFSRT), and each treatment field is treated with a separate accelerator, the above disadvantages of the subfractionated daily radiation therapy is eliminated. There are many radiobiological advantages for AFSRT as compared to the present conventional sequential radiation therapy of each fields including in 3-D conformal radiation therapy (3-DCRT) and IMRT. Furthermore, the radiation intensity of each accelerator treating each field is controlled to facilitate efficient IMRT. The accelerator that delivers radiation to a region that needs a higher dose rate is tuned to a higher dose rate and higher energy and the region that needs a lower dose, the dose rate is tuned to a lower energy and lower dose rate. The tumor is treated in 3-D conformity. Hence it is a 3-D conformal all filed synchronous intensity modulated radiation therapy (3-DC-AFS-IMRT) with multiple accelerators.

The AFSRT, AFS-3-DCRT, and 3-DC-AFS-IMRT, are much different than the present radiation therapy systems. In present IMRT systems increased monitor units and radiation filters are used for intensity modulation of the radiating beam. Higher the monitor units is used to radiate a filed, higher its leakage and scattered radiation and the total radiation received by the normal tissue surrounding the tumor and the tissue through which the radiating beam passes through towards the tumor site. This causes much more late complications from radiation therapy and second primary tumors as a result of earlier radiation to the primary tumor.

There are significant radiobiological difference between the interrupted subfractionated 30-33 cGy per field to give the total daily dose of 180-200 cGy and the simultaneous delivery 180-200-cGy to a tumor. In the latter instance, the daily subfractionated radiation therapy is eliminated. By doing so, the total cumulative radiation dose required to cure and or control a tumor is decreased. Most importantly, the patient comfort is increased significantly. To place a sick patient on a hard treatment table and to except not to make any movements regardless of the patient's discomfort is an unusual physician's prescription due to its need and circumstances.

The shape of cell survival curves for mammalian cells under photon or electron beams has an initial linear slope followed by a shoulder, ($\bullet D_1$) and a straight portion, the $\beta D_2$. The initial linear slope and shoulder is associated DNA breaks induced by the same electron at low dose rates while the steeper portion of the cell survival cure represents the two DNA breaks caused by two separate electrons. Within the daily fractionated radiation with subfractionation daily setup and multiple field interrupted treatment as described above with about 30 cGy dose rate to the tumor at any one time is dominated by the alpha$D_i$.

On the other hand, if the entire daily fractionated dose is delivered to the tumor simultaneously with multiple accelerators, the dose rate at the tumor will be four times higher, namely 180 to 200 cGy and hence much increased chances of inducing $\beta D_2$ like DNA breaks with multiple electrons.

In clinical radiation therapy with photons and electrons, the AFSRT of a tumor with multiple accelerators could lead to much improved tumor control probability. Theoretically one could foresee a five fold improvement by such treatment. In brief, its radiobiological effects in clinical radiation therapy such as on lethal, sublethal and potentially lethal DNA damage and repair associated tumor cure with lesser toxicity to normal tissue have great significance. Because of the simultaneous radiation to all the treatment fields and its higher dose rate effects, the total treatment dose for the entire course of treatment of a patient could be reduced. In this instance, the dependence on isoeffective radiation dose on duration and number of fractionation, the time and radiation dose relationship has changed from all forms of present conventional daily fractionated radiation therapy including the 3-DCRT. The 3-DC-AFS-IMRT has a higher tumor cure probability at lower total tumor dose.

In those patients surviving longer after radiation therapy by IMRT, the risk to develop second malignancies is increased by 0.5% than when they are treated by 3-DCRT. It is due to a larger volume of normal tissue is radiated to a lower dose by IMRT as compared to 3DCRT. In addition there is increased leakage and scattered radiation from increased monitor units used in IMRT. Due to beam modulation with a series of leaf sequences in IMRT the ratio of monitor units used are increased by a factor of 2 to 3. It is estimated that it causes an additional 0.25% second malignancies in patients surviving longer after IMRT. Thus there is an increase of 0.75% second malignancies after IMRT as compared to 3-DCRT. It is about twice the incidence of second malignancies observed with conventional radiation therapy (Hall, E. J. and Wuu, C. S. Radiation Induced Second Cancers: the Impact of 3-DCRT and IMRT, Int. J. Radiation Oncology, Biol. Phys., 56, p 83-88, 2003).

The increased risk for second malignancies is reduced by 3-DC-AFS-IMRT with multiple accelerators. 3-DC-AFS-IMRT is like 3-DCRT. The 3-DC-AFS-IMRT with multiple accelerators facilitates lower monitor units set up radiation to deliver the same tumor dose as in IMRT but without sacrificing the advantages of IMRT. The leakage and scattered radiation of IMRT is decreased. In this 3-DC-AFS-IMRT, semi automated blocks made of tungsten powder mixture or melted Cerrobend are used to make custom shaped treatment fields that are in conformity with the anatomy of the tumor and to exclude its surrounding normal tissue. This reduces about 2 to 4 times the scattered and leakage radiation as compared with the conventional IMRT with multileaf collimators. In 3-DC-AFS-IMRT with multiple accelerators and semi-automated custom blocks are made with tungsten powder mixture or melted Cerrobend.

Within this custom shaped larger treatment filed, dynamic variable smaller field size adjusting movements of the secondary collimators is made to make multiple smaller fields. It is combined with selective dose rate and energy adjustments of the accelerator. This provides intensity modulated beam delivery like in dynamic beam delivery with MLC; however it is with dynamic movements of the secondary collimators to make multiple smaller fields within the larger field of each beam directions. It does not involve partial absorption of the beam for intensity modulation. This provides a smoothly variable intensity profile as needed for the IMRT. In effect, it is a single field treatment and the monitor units needed to treat the whole field is the same as in conventional radiation therapy. Hence it reduces the monitor units needed to treat a filed as compared to the segmented, static multiple small fields within a larger filed treatment with MLC.

It also differs from the intensity modulating percent filtration of the beam as with dynamic beam delivery with MLC. Thus this field adjusting dynamic movement of the secondary collimator combined with dose rate and energy adjustments of the accelerator allows treating the tumor with lesser monitor units as compared to doing so with the MLC. Hence it generates lesser scatter and leakage radiation as compared to IMRT with MLC. The intensity of the radiation to a selected field is also modulated by selection of desired dose rates from each of the accelerators.

The higher monitor units used with conventional IMRT with MLC generates higher scattered and leakage radiation that causes increased radiation dose to normal tissue. The dynamic secondary collimator's field adjustments within a larger treatment field for each beam's intensity modulation combined with accelerator's dose rate and energy adjustments along with controlled speed of the secondary collimator's field size adjusting movements as in this invention enables to treat each of the treatment setup fields with much lesser monitor units as compared to doing so with MLC. It reduces the short term and long term complications of radiation therapy. It helps to eliminate or decrease the estimated incidence of additional 0.25% second malignancies among long term survivors as when treated by the present IMRT systems. It is further explained below by analysis of cancer incidence among the Japanese A-bomb survivors.

Data from Japanese A-bomb survivors who had acute whole body exposure of 200 cGy shows a four fold increase in bladder cancer in later life. Patients who survive 10 years or more after 48-67 Gy radiation treatment for prostate cancer have a relative risk (RR) of 1.8 for bladder cancer. Similarly, patients who survive 10 years or more after 30-80 Gy radiation treatment for cervical cancer have a RR of 5 for bladder cancer. This indicates that there is no difference in RR for bladder cancer over the dose range of 2 to 80 Gy.

In Japanese A-bomb survivors, the risk to develop solid tumors is linear up to 200 cGy acute exposure. The International Commission on Radiation Protection (ICRP) recommends the dose rate effectiveness factor (DREF) of 2 for low dose, low dose rate exposure. Allowing DREF as 2 and extrapolating from the Japanese A-Bomb survivors, the risk to develop solid tumors after fractionated radiation therapy could be considered as linear up to 400 cGy. (Hall, E. J. and Wuu, C. S. Radiation Induced Second Cancers: the Impact of 3D-CRT and IMRT, Int. J. Radiation Oncology, Biol. Phys., 56, p 83-88, 2003).

3-DC-AFSRT-IMRT with multiple accelerators is also advantageous in combined radiation and chemotherapy for cancer. In comparison with most chemotherapeutic agents, radiation is a weak carcinogen. In general, the chemotherapeutic agents produce more DNA lesions than the radiation; though it varies widely form one chemotherapeutic drug to another (Hall, E. J., Chemotherapeutic Agents from the Perspective of the Radiation Biologist, in Radiobiology for the Radiologist, Fifth Edition, p. 470-494, Lippencott, William and Wilkins, 2000). Concomitant radiation and chemotherapy is the choice of treatment for many solid tumors. Hence the carcinogenic effects of increased leakage and scattered radiation of IMRT has more clinical significance when combined radiation and chemotherapy is administered.

IMRT combined with chemotherapy with drugs like etoposide for carcinoma of the lung is a common clinical practice. Etoposide is known to cause secondary acute non-lymphocytic leukemia (ANLL). It is associated with translocation in band 11q23 and MLL gene rearrangement. It has a short latency period of 2-4 years and has no effective traditional chemotherapy. (Smith M. A., Rubenstein L, Anderson, J. R., Secondary Leukemia or mylodysplastic Syndrome after Treatment with epipodophyllotoxins, J. Clin Oncol. 17, p 569, 1999) In this scenario, an increase in leakage and scattered radiation to the normal tissue form IMRT is not a desirable option. To avoid later higher chances for the development of a second primary tumor, the dose to normal tissue needs to be kept as minimum as is possible.

Radiation Therapy Machine with Multiple Accelerators Mounted on to a Modified Conventional Accelerator's Gantry for Synchronous Treatment of all the Treatment Fields In this instance, parts of present conventional divergent beam medical linear accelerator is used to make a synchronous all field radiation therapy machine with multiple accelerator units. It is combined with a kV CT for IGRT. The main gantry of a conventional medical accelerator is modified to hold multiple accelerators with the treatment head and accessory holder. Extensions to the gantry are made to attach additional accelerators and the treatment head with the accessory holder. Each of the accelerator units contains all the parts of a conventional medical linear accelerator namely the accelerator waveguide, treatment head with the bending magnet, target, dose monitors and other related accessories and the accessory holder. Alternatively, split electron beams from a racetrack microtron or a simpler microtron is guided into each smaller medical linear accelerators of the multiple accelerator incorporated radiation therapy system of this invention.

This accelerator system is placed behind a kV CT. With the extension attached to the main rotating gantry of a conventional medical linear accelerator. When a combination of four accelerators is attached to a partially rotating gantry at 90° apart, a 45° forward or backward rotation is sufficient to enable a combined 360° gantry rotation. The 45° gantry rotation is easier for this multi accelerator system than a complete 360° rotation. However, these gantries can make more than 45° rotations. It allows treating a patient from any desirable angles. The extension gantry is attached horizontally when the main gantry is perpendicular, at 0°. Each of these gantries holds two medical accelerators, one at each ends. These gantries with the treatment heads and accessory holders are made to rotate around the CT's table top with flat table top insert when they are extended towards the accelerator system through the CT-gantry's opening. The accelerator components including the electron accelerating waveguide, bending magnet, field defining primary and secondary collimators, dose monitors and the accessory mount that holds the custom shaped blocks all are the same as in a conventional medical linear accelerator. Likewise the electric and electronic components including the thyrotron, power supplies, cooling systems, vacuum pumps and other accessories including the dose monitors are all the same as in a conventional medical linear accelerator. It is an adaptation of the conventional medical linear accelerator into a multi-medical linear accelerator system for simultaneous treatment of all the treatment fields at one time to avoid interrupted subfractionated daily fractionated radiation therapy. Like in a conventional medical accelerator, both gantries are isocentrically mounted but with the capability to extend individual accelerators plus or minus 20 cm to make adjustments for the SSD method of treatment. To make this extension or retraction of the accelerator unit with the treatment head, each accelerator with its treatment head is made to slide on a gantry extending and retracting teethed bar that engage with the teethed slots in a fixed second bar within the gantry. When the accelerators are in isocentric position, isocentric SAD and rotational treatment methods are possible. When the treatment heads on the gantry are moved to adjust the SSD, the SSD method of treatment is feasible. To maintain the treatment position of the patient placed on the CT's table top with the flat table top insert after the kV CT imaging for IGRT is done no additional CT-table positional changes are made during the radiation therapy.

The first accelerator unit is mounted onto the gantry as in a conventional medical linear accelerator. The second accelerator is mounted at the end of this main gantry where the counterweight or a beam shield is attached to a conventional medical accelerator's gantry. In this instance, the counter weight or the beam shield is removed and in its place the second accelerator with its treatment head and the accessory holder are mounted. In addition, modifications are made for moving the gantry extending and retracting teethed bar. It is made to slide on a fixed second bar with a motor driven drive mechanism. Without the gantry's extension or retraction the accelerator treatment heads are at isocenter distance of 100 cm. Forward or backward rotation of one of the engaging teeth and slot on these bars moves the accelerator and the treatment head 1 cm forward or backward. The maximum forward or backward travel distance of the sliding teethed bar on the fixed second bar is limited to 20 cm. A 20 cm forward extension or 20 cm backward retraction of the sliding gantry extending and retracting teethed bar with the accelerator head and the accessory mount increases the SSD to 120 cm or decreases to SSD to 80 cm. If a lesser forward or backward extension or retraction is elected then these SSD distances will vary accordingly. This variable SSD setup capability along with the capability to select the isocenter distance of 100 cm allows treating a patient either by SSD method or by SAD method. A bellowed connection of the gantry between its cut portions facilitates these extending and retracting movements of the accelerator's treatment head with the accessory mount.

As an alternative to the above partially or fully rotating gantry with multiple accelerators, non-rotating gantry with multiple accelerators capable of deflection of the electron beam exiting from the accelerator's waveguide by deflection magnets before it strikes onto the target to produce the photon beam is used to make effective rotational beam for the treatment of multiple fields from multiple beam directions. In this instance, the gantry with multiple accelerators does not rotate. In the case of a radiation therapy machine with four accelerator combination, the accelerators are attached to the gantry at 90° apart, at 0, 90, 180 and 270°. The microwave power to the accelerating wave guide is supplied from shared microwave power generating magnetrons or klystrons by splitting the microwave power from the source and conducting it through microwave transmitting tubes in the gantry and the gantry extensions holding the accelerators. These accelerator units are made to deliver radiation from 0 to 45 and 0 to 315°, from 90° to 135° and 45°, from 180° to 225° and 135°, and from 270° to 315° and 225° ranges by deflection of the electron beam exiting from the accelerator waveguide by deflection magnets before it strikes onto the target to produce the photon beam. If a field is to be treated from 45° angle ranges, then the electron beam exiting from the waveguide of the accelerators either at 0° or at 90° is deflected within this 45° range of treatment directions. If one of the beams is elected as from 45° angles, the electron beam from the 0° accelerator is deflected 45°+, that is in clockwise direction or the electron beam from the 90° accelerator is deflected −45°−, which is in anticlockwise direction. If one of the treatment angles is elected as 200, the electron beam from the 0° accelerator is deflected 20°+, that is in clockwise direction. If one of the treatment angles is elected as 340° angles, the electron beam from the 0° accelerator is deflected 20°−, that is in anticlockwise direction. In other words the beam directions from each of the accelerators can be adjusted 45° either forward or backward by electronic scanning of the exit beam from the accelerator's waveguide. With four accelerators, all mounted to a fixed gantry and with such forward or backward scanning of the electron beam exiting from the waveguide enables the treatment of a patient on the treatment table at any desired angle without rotating the gantry.

Like with the fully or partially rotating gantry with multiple accelerators, in this instance also the radiation beam from all the accelerators converges at the tumor site simultaneously. It delivers high dose rate radiation to the tumor. When the treatment is rendered with four accelerator combination, it is like the conventional four fields IMRT but with the exception of radiation intensity is modulated by selective beam energies and dose rate as needed for each field and treating all the fields concurrently. If it is an eight accelerators combined radiation therapy system, then it is an eight field synchronous radiation therapy machine. C-band and X-band accelerators are very light weight and very small accelerators. Hence for the eight accelerator combination, the C-band or X-band accelerators are used.

Alternative to a conventional medical linear accelerator, a conventional race track microtron with energies ranging from 4-15 MV electron and mounted within the main stationary gantry or adjacent to it is used as the electron accelerating unit. The electron beam is split by means of electron splitting magnets and guided to each treatment heads by means of guidance and bending magnets to produce electron or photon energies ranging from 4-15 MV as in conventional medical accelerators.

Split Beam from a Race-Track Microtron or a Microtron and its Acceleration in Smaller Waveguides Incorporated Linear Accelerators for a Multiple Linear Accelerators Incorporated Radiation Therapy System In a racetrack microtron, the initial electron beam from a smaller linear accelerator's waveguide is further accelerated under magnetic force and according to the microtron principles. To make compact multiple medical linear accelerators incorporated into a single radiation therapy system as in this invention, the methods used in racetrack microtron is modified. After a few revolutions of the electron beam in a smaller racetrack microtron, the beam is split into multiple beams and thy are guided into each of the waveguides on the multiple linear accelerator system to increase the energy ranging from 4 to 15 MV or 6-15 MV. Similar split beams are also taken from a simpler microtron but with lesser initial electron beam energy. Because of the electron beam from a single source is conducted to multiple accelerators, the accelerator gantry extension is not feasible and hence only isocentric, SAD method of treatment is feasible in this arrangement of multiple treatment heads incorporated medical accelerator system.

Microwave Power

The microwave power source for this multi-accelerator system is a magnetron or a klystron. From this microwave power source microwave is transmitted into a circular microwave conducting tube with microwave power outlet openings. From the microwave conducting tube microwave power is extracted through its microwave power outlet openings and it is conducted to each accelerator through flexible microwave power transmission guides.

Radiation Therapy Simulation with kV-CT Combined with Portal Imaging with Multiple Accelerators For combined kV-CT and portal image guided treatment simulation (CTPIGS), the CT-scan images are first taken with kV-CT with the patient in treatment position and with markers attached to the patient and to the patient's immobilization devices. The patient is placed on the CT-table. Afterwards, the immobilization device is attached to the patient. Markers placed to the patient, to the immobilization device and to the CT-table are then checked for its correlation with anatomical markers on the patient. Afterwards, CT scout scans and CT-transverse, coronal or sagittal scans are taken. The CT-scan's video image projected onto the CT-monitor for the correct setup of the patient on the CT-table in relation to the markers attached to the patient, to the immobilization device and to the CT-table is checked and if corrections are needed to the patient's positioning on the CT-table, then such corrections are made and the CT is repeated. With correct patient's positioning on the CT-table, CT-table with the patient is advanced towards the accelerator that is just behind the CT-gantry opening. MV port-films are then taken to verify the accuracy of the treatment position in relation to CT-patient positioning. This is correlated with the simulation films taken with a conventional simulator. The simulation films taken with a conventional simulator and its correlation with the kV-CT-images and MV-port films are checked. The Styrofoam cut is made with the aid of the markers made on to the simulation films. The semi automated blocks made from tungsten powder mixture (TPMB) or from the melted Cerrobend (MCB) with the aid of the Styrofoam cut as described later. The treatment fields in correlation with the markings on the patient, on the immobilization device and on the CT table are checked with the semi automated blocks in position at the tertiary block holding tray of the accelerator. The treatment fields for each of the multiple accelerators are checked with the semi-automated custom field blocks on block holding tray by combined kV-CT and MV-port films methods as described earlier. Final adjustments to bring the treatment fields in conformity with the simulation fields and the kV-CT and MV-port checks are made if necessary as part of simulation. Correlation with shaped treatment fields and the markers placed on the patient, immobilization device and on the CT table as visualized in projected daily scout scans and or transverse, coronal or sagittal CT-scans are used as part of the IGRT. It is enhanced by frequent treatment port verifications with MV-port films.

Computed Tomography (CT) Combined Radiation Therapy Machine with Multiple Accelerators for 3-DC-AFS-IMRT and Image Guided Radiation Therapy (IGRT).

In this modified version of CT combined radiation therapy machine for 3-DC-AFS-IMRT and IGRT, the radiation therapy machine with multiple accelerators attached to the same gantry is placed in back of a CT-scanner. The radiation therapy machine with its gantry holding multiple accelerators is installed behind the CT-scanner. The CT-table is also used as the treatment table. It extends from the CT-scanner towards the multi-accelerator radiation therapy machine. The gantry with multiple accelerators does not rotate as in a conventional medical accelerator.

The CT-scanner is used for the imaging and as a simulator to determine the treatment position of a patient on the CT-table. After the treatment position is determined, the patient is placed under an immobilization device that does not cause CT-artifacts. The patient is scanned as immobilized and markers are placed on the immobilization device and on the patient as needed. Such markers are made to represent the anterior and lateral isocentric lines and other landmarks. The final CT images taken with the patient on treatment position are used for the treatment planning. At the site of each treatment fields, windows are cut from the immobilization devise to preserve the skin sparing qualities of the radiation beam. Before each day's fractionated radiation therapy, the treatment position and the tumor localization are again verified by two or three CT imaging and by checking its correlation with the previously established anterior and lateral isocenters and other landmarks. After making any fine turning adjustments in patient's positioning if needed and repeat verification of the adjustments made by repeat CT imaging to correlate with the treatment fields, the CT table with the patient is advanced towards the multi-accelerator radiation therapy machine. The angle of each accelerator's treatment beam is adjusted with beam deflection magnets as described before. All the treatment fields' alignment with the radiation beam is also checked by light field that correlates with the radiation beam as in conventional radiation therapy. The light is deflected mechanically as it to correlate with the deflected radiation beam that exits from the accelerator. The daily dose of fractionated radiation is given by synchronous activation of all the accelerators to treat all the fields simultaneously. This constitutes the daily fractionated 3-DC-AFS-IMRT/IGRT.

The kilovolt computed tomography (kV-CT) eliminates additional megavoltage radiation to normal tissue that is within and outside the treatment fields. It is a significant advantage for treating a patient with cancer as compared to megavoltage computed tomography (MVCT).

As described earlier, the 3-DC-AFS-IMRT and IGRT machine of this invention is aimed to reduce the radiation to normal tissue without compromising the advanced treatment capabilities of IMRT and IGRT. By reducing the radiation to the normal tissue by this KV-CT combined 3-DC-AFS-IMRT and IGRT machine, the late complications of radiation therapy including the development of second primary tumors is minimized.

Low-Cost 3-DC-AFS-IMRT and IGRT Machine

Low-Cost KV-CT for Imaging

Older version medical accelerators that are purchased at their scrap metal values. They are converted into a radiation therapy system, with multiple accelerators attached to a single gantry. Likewise, old CT scanners are purchased at their scrap metal value and incorporated with the multiple accelerator radiation therapy system. This combined multiple accelerators attached to a single gantry and the CT scanner facilitates advanced affordable IMRT and IGRT to places where such capabilities are not available.

Tertiary Collimation for 3-DCRT and IMRT with Semi-Automated Custom Field Shaping Blocks Made of Tungsten Powder Xu, T. et al described a method for making radiation beam intensity modulating filters with a mixture of tungsten powder, silicon rubber and paraffin. This radiation beam attenuating mixture was first shaped to a uniform thickness in a cup and then its thickness was modified manually by pressing with an array of 16×16 pistons. The excess of this mixture was allowed to flow out of the container. The shaped filter had varying thickness. After the filter was shaped to varying thickness, it was separated from the cup and placed on the block holding tray of the accelerator head and tested as a beam intensity modulator. Its beam transmission characteristics were like that of a beam intensity modulating MLC.

In this invention, tungsten powder is used to make custom shaped block for radiation therapy. Here the primary goal is to make custom shaped block with tungsten powder and not to make beam intensity modulating filters. The primary and secondary collimators of the accelerator head are used to define the initial field. The tungsten powder block (TPB) is used as the tertiary collimator.

The tungsten powder is easily dispensable into any container of any shape and form like into a plastic bag or into a container formed out of a Styrofoam cut like those used for custom shaped Cerrobend block making. By applying modest pressure, it is easily pushed from an interconnecting bottom reservoir into an upper reservoir. For semi automated tungsten powder block making, tungsten powder is held in a reservoir below the block holding tray of the accessory mount, the tungsten powder holding bottom reservoir. The tungsten powder block is formed in a block forming Styrofoam cut inserted into a tungsten powder block forming reservoir held at the top of the block holding tray of the accessory mount, the upper tungsten powder block forming reservoir. The upper tungsten powder block-forming reservoir is shaped to hold the Styrofoam cut like the one used to make custom Cerrobend block for radiation therapy. In this instance, the center and lateral Styrofoam cuts are used to shape the custom block with tungsten powder. A container is made to hold the Styrofoam cut on top of the block holding tray. It is a 20.5× 20.5×12.5 cm sized square container. It is made of four side walls and top and bottom covers. At three sides at the top of this container is equipped with engaging slots to slide in a 0.5 cm thick Lucite top cover plate from the other open side. This top cover is marked with centering cross hair lines that are in alignment with the cross hair makings of the reticule below the primary and secondary field shaping collimators. They are used for fixing the central and the lateral portions of the Styrofoam cuts beneath it as centered to the central axis and along the divergence of the radiating beam. Through boreholes drilled on to this tope cover, fixing Lucite nails are inserted to the Styrofoam cuts along the centering lines marked on the Styrofoam cuts. The bottom cover plate of the tungsten powder block holding container is formed by a 20×20×0.5 cm Lucite plate when it is inserted with the block forming Styrofoam cuts. Before inserting the central and the lateral Styrofoam cuts into the tungsten block forming container, they are fitted on this 20×20×0.5 cm Lucite tray as centered to the central axis of the divergent beam. The tungsten block forming container is mounted on to a 5×27.5×0.5 cm square bottom Lucite mount with 3 cm outwardly projecting edges. Several boreholes are drilled onto the outwardly projecting portion of this bottom Lucite mount. Through corresponding boreholes drilled onto the block holding tray of the accessory mount, the tungsten powder block holding container is fixed on to it with Lucite nuts and bolt. Cross hair lines centering with the central axis and divergence of the beam are marked on top of the block holding tray of the accessory mount. It is marked as in alignment with the cross hair makings of the reticule below the primary and secondary field shaping collimators. These markings of the cross hair lines are used for placement of the tungsten powder block forming container on top of the block holding tray of the accessory mount as centered with the central axis and the divergence of the radiating beam. A 20×20×0.5 cm Lucite plate is shred by the tungsten powder block forming container and the Styrofoam cuts. It is fitted with Lucite nails along the centering lines of the divergent radiating beam. These Lucite nails are used to fix the Styrofoam cuts firmly onto this Lucite plate. Before inserting the Styrofoam cuts into the tungsten powder block forming tray, they are fixed on to this Lucite plate as centered to the central axis and the divergence of the radiating beam with the aid of the centering lines as projected from the reticule. These lines are etched onto this Lucite plate. When this Styrofoam cuts holding Lucite plate with the Styrofoam cuts as fixed onto it is inserted into the tungsten powder block forming container, this Lucite plate also becomes the bottom cover of the tungsten powder block forming container. Inlet-outlet openings are drilled on to this 20×20×0.5 cm Lucite plate, onto the block holding tray of the accessory mount and on top cover of the tungsten powder holding bottom reservoir's Lucite plate. They function as interconnecting openings for moving the tungsten powder into the tungsten powder block forming container on top of the block holding tray or into the tungsten powder holding bottom reservoir below the block holding tray.

The openings in the bottom cover plate of the tungsten powder block forming container, block holding tray of the accessory mount and the tungsten powder holding bottom reservoir's upper cover are interconnected with tightly fitting elastic plastic tubes. The openings at the top of the block holding tray of the accessory mount are fitted with tightly fitting rubber seals with central openings. These rubber seals projects 0.5 cm upwards from the top of the block holding tray of the accessory mount. The bottom cover plate of the tungsten powder block forming container with the tungsten powder block forming Styrofoam cut is inserted into the tungsten powder block forming container as aligned with these rubber seals. With these openings centered and tightly secured on top of the block holding tray of the accessory holder, aligned interconnecting openings are established between the tungsten powder block forming container, block holding tray of the accessory mount and the tungsten powder holding bottom reservoir. The tightly fitting rubber seals with central openings at the top of the block holding tray of the accessory mount prevent any leakage of the tungsten powder during its passage to and from the tungsten powder block forming container.

A 20×20×12 cm sized Styrofoam can be tightly fitted in to the tungsten powder block forming container. Styrofoam cuts are made similar to the custom Cerrobend block making Styrofoam cuts from a standard 20×20×12 cm sized Styrofoam block with the aid of a Styrofoam cutter. To make the tungsten powder block, the mid Styrofoam cut is removed and the space occupied by it is filled with tungsten powder.

To fill the space occupied by the mid Styrofoam cut semi-automatically, first the central and the lateral Styrofoam cuts are fitted on to the tungsten powder block forming container's 20×20×0.5 cm bottom cover plate as centered to the central axis of the divergent beam with the aid of the centering cross hair markers. This Lucite plate with the Styrofoam cut is then placed on to another 20×20×0.5 cm sized another Lucite plate but with no openings drilled onto it. After removing the top cover plate of the tungsten powder block forming container, the block forming Styrofoam cuts on these Lucite plates is inserted into the tungsten powder block forming container. Afterwards the 20×20×0.5 cm Lucite plate without openings is pulled out of the tungsten powder block forming container. It opens the openings in the bottom cover plate of the tungsten powder block forming container. Those openings are now in continuity with the openings in the block holding tray of the accessory holder and with those in the top cover plate of the tungsten powder holding bottom reservoir. Tungsten powder block is formed within the space occupied by the mid Styrofoam cut when the tungsten powder from the tungsten powder holding bottom reservoir is pushed into it by inserting pressure on to the tungsten powder holding bottom reservoir. Such a block is shaped as to conform to the divergence of the beam. The Styrofoam is cut in conformity with the slope of the diverging beam. It provides a slanting downward slope according to the beam divergence. When the pressure on the tungsten powder holding bottom reservoir is released, the flow of the tungsten powder is reversed; in this instance, by gravity the tungsten powder from the tungsten powder block forming space in the Styrofoam cut in the tungsten powder block forming container drops back into the tungsten powder holding bottom reservoir through the interconnecting openings in this block forming device. When the Styrofoam cut is empty from the tungsten powder, the 20×20×0.5 cm Lucite plate without openings is reinserted back to its place, at the bottom of the 20×20×0.5 cm bottom cover plate of the tungsten powder block forming container with openings. Then the Styrofoam cut along with the plate with openings on which it is fixed and the plate without openings and placed at the bottom of the plate with opening are pulled out. This removes the Styrofoam cut from the tungsten powder block forming container without spillage of the tungsten powder.

On the block holding tray, 12 two and a half cm sized holes are drilled to allow the passage of the tungsten powder upwards or downwards. They are drilled within the space representing the mid Styrofoam cut. It gives 12 openings around the central Styrofoam cut that is inserted as aligned to the centering cross hair markings on top of the bottom plate of the tungsten powder block forming container. These openings are in alignment with similar openings in the bottom plate of the tungsten powder block forming container and the tungsten powder holding bottom reservoir as described before. Through these aligned openings, tungsten powder is pushed from the bottom reservoir to the tungsten powder block forming container at the top of the block holding tray of the accessory mount until the space occupied by the mid Styrofoam cut is filled with tungsten powder to form the custom shaped tungsten powder block. After treating a patient with the aid of this custom shaped tungsten powder block, the tungsten powder is removed from the tungsten powder block forming container by gravity drop of the tungsten powder back into the tungsten powder holding bottom reservoir by releasing the pressure to the tungsten powder holding bottom reservoir. This process of custom tungsten powder block making is repeated each time a new patient is setup for the treatment.

The central Styrofoam cut is used to make the custom shaped tungsten block's open shaped field for the treatment. It is fixed on to the block forming tray as centered to the projected cross hairs of the reticule. The center relative to the horizontal and the vertical dimension of the diverging beam at the bottom of the center of the Styrofoam cut is marked. It is cut in conformity with the diverging beam. Using these horizontal and vertical lines marked at the bottom of the central Styrofoam cut, it is inserted on to the Lucite nails on the block holding tray as centered to the central axis of the beam and in conformity to the projected crosshairs of the reticule and divergence of the beam. It is thus centered and fixed on to the block holding tray.

The measurement of transmission of 6 and 10 MV radiation beam through the central Styrofoam cut so fixed onto the block holding tray shows less than 1% attenuation of 6 and 10 MV beams mostly almost to zero percent.

At the under surface of the accessory holder of the accelerator's treatment head tungsten powder holding reservoirs are attached. To keep them away from the diverging beam's path, they are made as a 10×20×10 cm sized elastic container. It extends to the under surface of the block holding tray when it is inserted on to the accessory holder. There are 12, two and a half cm sized openings in mid Styrofoam cut region on the block holding tray. They are in coincidence with similar holes at the top of the block holding tray. These openings connect with the upper tungsten powder block forming container and the lower tungsten powder holding reservoir. The bottom of the bottom reservoir is mounted on top of 10×20×1 cm steel plate. The outer ends of these plates are connected to the upper side of the block holding tray by means of 10 cm long 2 cm diameter rods with groves for the passage of a fitting nut. The top and bottom of this length adjusting rods are fitted with nuts for control of the rods upward and downward travel on the rod. There is one such rod at each corner ends of this bottom reservoir holding tray. Its upper end is fitted onto the block holding tray. This entire system of the bottom tungsten powder holding reservoir is enclosed in a bellowed container that moves with this reservoir upwards or downwards based upon volume adjusting rotations of the connecting rods.

Clockwise and counter clockwise hand or motor driven rotations of all the four rods with the nut simultaneously pushes the elastic tungsten powder containing reservoir upwards or downwards. For hand driven upward or downward movement of these reservoirs, winding mechanism are attached at its corner edges. It is wound like winding of a clock. The reservoirs are lifted or lowered by clockwise or counterclockwise winding of this winding mechanism. Consequently, its content, the tungsten powder is pushed upwards or downwards. When it is pushed upwards by the clockwise rotation of the rod in the road and nut mechanism, the tungsten powder is pushed upwards into the tungsten powder block forming container at the top of the block holding tray. The level of such filling with the tungsten powder into the block forming container is controlled by sensors that controls the revolution of the rods by the motor or by the hand. Such sensors are attached to the under surface of the top plate of the block forming container. When the connecting rod's rotation is counterclockwise the plate holding the lower reservoirs are pushed downwards. It expands the elastic lower reservoir and hence the tungsten powder drops into the lower reservoir. It empties the block forming container from the tungsten powder. When it is empty, the sensors placed at the bottom plates of the block forming container sends signals to the motor to stop rotation of the connecting rod and nut. When the hand driven winding mechanism is used, the sensors sends an alarm signal to stop the winding.

In summary, for custom block making to shape a treatment field, the tungsten powder block forming container is removed from the top side of the block holding tray and it is fitted with the central and lateral Styrofoam cuts as centered to the central axis of the diverging beam as described earlier. It is then tightly covered with the tungsten block forming container and inserted to the accelerator's accessory holder. For each patient, shaped block making Styrofoam cuts are made and fixed on to the block holding tray as above. By pushing the tungsten powder from the lower reservoir into the empty space in the Styrofoam cut in the tungsten powder block making container the semi automated tungsten powder block making is done. After treating a patient, the Styrofoam cut is emptied automatically and the block holding tray with the empty Styrofoam cut is removed. A patient's custom Styrofoam cut fixed on to the block holding tray is repeatedly used for the daily radiation treatment of that patient. For treating the next patient, that patient's block holding tray with the Styrofoam cut is inserted to the accelerator's accessory holder and the semi automated tungsten powder block making is repeated and the patient is treated. This process is repeated for the treatment of each patient. It is not a lengthy or tedious process. It has much lesser scatter, leakage and penumbra radiation than when MLCs are used for 3-DCRT and IMRT.

Custom Field Shaping Blocks Made of Tungsten Powder without Automated Filling of the Styrofoam Cut with Tungsten Powder In this case, Styrofoam cuts are made and it's central and lateral cuts are fixed on to the block holding tray as above. The empty space formed between the central and the lateral Styrofoam cuts by removing the medial Styrofoam cut is filled with easily dispensable tungsten powder and it is sealed before the Styrofoam cut is inserted into the tungsten powder block forming container on the top side of the block holding tray. For each patient, after shaped block making Styrofoam cuts are made, the empty space in the Styrofoam cut is filled with in the tungsten powder before this Styrofoam cuts and tungsten powder block is inserted into the tungsten powder block making container. It is then used as the custom block to treat that particular patient for whom this block was made. After treating a patient, the Styrofoam cut with the tungsten powder is removed from the tungsten powder block making container. A patient's custom Styrofoam cut with tungsten powder block in the space occupied by the mid Styrofoam cut is used repeatedly for the daily radiation treatment of that patient. For treating the next patient that patient's block holding tray with the Styrofoam cut and tungsten powder as described above is inserted to the accelerator's accessory holder and that patient is then treated. This process is repeated for the treatment of each patient. It is not a lengthy or tedious process. It has much lesser scatter, leakage and penumbra radiation than when MLCs are used for 3-DCRT and IMRT.

Tertiary Collimation with Conventional Cerrobend Blocks for Beam Shaping

Alternative to the multi leave collimator of this invention, conventional Cerrobend blocks for beam shaping also could be used with the divergent beam accelerators. However, it would be more labor intensive. Making the Cerrobend blocks for each patient is tedious. On the other hand the option to use the Cerrobend block for radiation therapy field shaping helps to reduce the costs of this still far advanced multi-accelerator radiation therapy machine with kV-CT.

When a conventional multi leave collimator is used, the quality of the entire radiation therapy depends on precise computer controlled moving of the multi leaves. The cost of a multi leave collimator can approach to the cost of a lesser expensive medical accelerator. Likewise, its maintenance is also very expensive. There are many places where such costs are not affordable. There are also many places where maintenance of such computer controlled precision operation of the multi leave collimator is difficult after purchase. In such places, the Cerrobend beam shaping blocks eliminates reliance to flawless operation of each of the leaves of a multi leave collimator. Perfect matching of each of the leave's tongue and blade and edge of a multi leave collimator is essential to minimize the leakage radiation, especially to normal tissue. Hence the Cerrobend block is more adaptable to places where the cost and maintenance of a conventional multi leave collimator is simply not affordable.

In this invention, alternative to the conventional Cerrobend blocks, a melted Cerrobend system is devised to overcome the cost and to minimize the computer controlled reliance on its operation. Its cost-effectiveness and efficiency is applicable to every where.

3-DC IMRT-IGRT Custom Filed Shaping with Melted Cerrobend Block (MCB)

Like when custom shaped solid Cerrobend blocks is used with the primary and secondary collimators of the accelerator to define the initial field, the melted Cerrobend block (MCB) is also used with the accelerator's primary and secondary collimators to define the initial filed size. Like the conventional solid Cerrobend block is a tertiary collimator, the melted Cerrobend block-forming device is a tertiary field shaping collimator. However, it is much different than the conventional solid Cerrobend block. Like the radiation field is shaped with the MLC the MCB shapes the field for treatment when the patient is setup for the treatment.

Because of the low 70° C. melting point of Cerrobend, it can be kept in liquid form easily in reservoirs with heating units. The tertiary block holding tray is modified to hold the melted Cerrobend block. The reservoir is divided into upper and lower compartments. The upper reservoir compartment is further divided into a block forming peripheral portion and a central inner radiation filed defining area. The peripheral filed defining area represents the usual block forming Styrofoam mid cut. However, it is a fixed 15×15×12.5 cm square cup like container made of 1 cm thick steel plates at its four side walls. Alternatively it is made from any other suitable metal plates that can function both as a heat conducting unit and as a block forming container. It is shaped similar to a custom Cerrobend block making mid Styrofoam cut with slanting downward slope for beam divergence. The tope cover plate of this container is made of 0.5 cm thick Lucite. An 11×11 cm open area centered to the central axis of the beam is cut in the bottom plate of this container giving 4 cm width and 15 cm long side covers to the remaining portion of the bottom plate. Three two and a half cm sized circular openings are made at each of these remaining side covers of the bottom plate to give 12 such openings for the back and forth flow of the melted Cerrobend into the cup and into the lower Cerrobend reservoir. This square cup-shaped container with the slanting slope for beam divergence is inverted to face its broader downside area to the tertiary block holding tray. It is centered to the divergent radiating beam's axis as it projects on the block holding tray. Thus the Lucite plate forms the top plate of this container and the plate with the 11×11 cm open area forms the bottom cover of this container. The bottom edges of the bottom plates of this Cerrobend holding cup are fitted with three mm sized Lucite rods that run along the periphery of this cup and the projected crosshair lines of the reticule. As usual, the reticule is placed just below the lower jaw of the accelerator head. These Lucite rods slide into the groves in the block holding tray. These groves on the block holding tray are made in conformity with the positions of the Lucite rods at the bottom of the melted Cerrobend holding inverted cup. They hold the melted Cerrobend holding cup in centered position on the block holding tray. On the block holding tray locking latches are inserted to hold the melted Cerrobend holding cup in place. These locking latches on the block holding tray have locking extensions that is inserted into the corresponding latch holding extensions at the lower corner edges of the melted Cerrobend holding cup. This latching mechanism holds the melting Cerrobend holding cup in place on the block holding tray.

The central radiation field defining area represents the central Styrofoam cut made in the process of making a custom Cerrobend block. To make a conventional solid Cerrobend field shaping block, the cavity formed by removing the middle Styrofoam cut is filled with melted Cerrobend and the Cerrobend is cooled to room temperature. The inner Styrofoam cut is kept in place when the melted Cerrobend is poured into the cavity formed by removal of the middle Styrofoam cut. It prevents the flow of melted Cerrobend into the area covered by the inner Styrofoam cut which represents the custom shaped field of radiation. After the Cerrobend is cooled and the solid block is formed, this radiation field shaping inner Styrofoam cut is removed. Now the inner Styrofoam cut area becomes an open shaped field for radiation.

This invention's custom block making differs from conventional custom block making. Styrofoam cuts are made from a 20×20×12 cm Styrofoam block. The central field shaping Styrofoam cut is fixed on to the block forming tray to shape the radiating field. There is only about less than 1% attenuation of 6 and 10 MV photons is transmitted by such radiation field defining inner Styrofoam cut when it is in the path of the beam. On the block holding tray, it is fixed along the projected cross hairs of the reticule that is inserted below the lower jaws. For its fixation on the block holding tray, it is equipped with four fixing Lucite nails, one on each projected crosshair lines. The center relative to the horizontal and the vertical dimension of the diverging beam at the bottom of the center Styrofoam cut is marked. It is cut along the divergence of the beam. Using these horizontal and vertical lines marked at the bottom of the central Styrofoam cut, it is centered and inserted on to the Lucite nails along the projected crosshairs lines on the block holding tray. It is thus fixed on to the block holding tray as in conformity with the path of the diverging beam.

After fixing the inner Styrofoam cut on the block holding tray as centered to the divergent beam, the center relative to the horizontal and the vertical lines projected from the reticule at the top of the center Styrofoam cut is checked for its conformity with the divergent beam. After the center and the middle Styrofoam cuts were made, centering horizontal and vertical lines are marked at their top and bottom. Using these horizontal and vertical lines at the top of the central Styrofoam cut, it's centering on the block holding tray is double checked by inspecting its coincidence with the reticule's projected crosshairs lines on the top of the central Styrofoam cut. If fine adjustments are needed, it is made by wiggling the Styrofoam cut towards the cross hair lines to bring the cross hair lines marked on the Styrofoam cut and that projected from the reticule.

The measurement of transmission of 6 and 10 MV radiation beam through the central Styrofoam cut so fixed onto the block holding tray shows only about 1% blocking of 6 MV and 10 MV beams. After fixing the central Styrofoam cut in the block holding tray, the block forming cup that represents a universal mid Styrofoam cut's cavity is also inserted onto the block holding tray as described before. At the under surface of the block holding tray Cerrobend melting and the melted Cerrobend holding reservoirs are attached. To keep them away from the diverging beam's path, they are attached outside the corresponding edges of the inverted cup as it is seen from the under side of the block holding tray. These reservoirs are made as square 10×25×10 cm sized elastic containers with heating coils. One of each of these containers fits into the outer undersides of the block holding tray. There are three two and a half cm sized openings in each of these reservoirs. They are at corresponding distances with the openings on the melted Cerrobend forming cup's bottom cover. These openings are aligned with those of the melted Cerrobend holding cup inserted at the topside of the block holding tray. They are interconnected with interconnecting plugs with central openings. These reservoirs are kept at 70° C. to keep the Cerrobend as melted. Each one of these reservoirs is mounted on top of 10×10×1 cm steel plates. The outer ends of these plates are connected to the upper side of the block holding tray by means of 10 cm long 2 cm diameter screw like rods. The top and bottom of this length adjusting screw-like rods are fitted with nuts for control of the rods upward and downward travel of the rod. There is one such rod at each corner ends of this reservoir holding tray.

Clockwise and counter clockwise hand or motor driven rotations of all the four rods on the screw and nut mechanism simultaneously pushes the elastic heated Cerrobend containing reservoirs upwards or downwards. For hand driven upward or downward movement of these reservoirs, winding mechanism are attached at its corner edges. It is wound like winding of a clock. The reservoirs are lifted or lowered by clockwise or anticlockwise winding of this winding mechanism. Consequently, its content, the melted Cerrobend is squeezed upwards or downwards. When it is squeezed upwards by the clockwise rotation of the screw-like rod in the road and nut mechanism, the direction of the flow of melted Cerrobend is upwards into the block forming cup. The level of such filling with the melted Cerrobend into the block forming cup is controlled by sensors that controls the revolution of the rods by the motor. Such sensors are attached to the under surface of the top plate of the block forming cup. When the screw-like rod's rotation is counterclockwise the plate holding the lower reservoirs are pushed downwards. It expands the elastic lower reservoirs and hence the direction of the flow of melted Cerrobend is downwards, into the melted Cerrobend holding lower reservoirs. It empties the block forming cup from the melted Cerrobend. When it is empty, the sensors placed at the bottom plates of the block forming cup sends signal to the motor to stop its rotation of the screw-like rod in the rod and nut mechanism. After treatment of a patient, the block forming cup and the Styrofoam inner cut are removed from the block forming tray. The inner Styrofoam cut is reusable for continued daily radiation treatment of the same patient for whom it was made until another custom field shaping is needed. In preparation to treat another patient, this cycle of block making with melted Cerrobend is repeated.

In this invention, beam's intensity modulation for IMRT is by means of using multiple accelerators mounted on to the same gantry and all working together for simultaneous radiation to the tumor from multiple fields. The dose rate and energy of each of these accelerators are selected as needed for the intensity modulation. Additionally, the treating field size is varied for each accelerator's to suit the beam's intensity modulated treatment volume. After treatment of a patient, the block forming cup and the Styrofoam inner cut are removed from the block forming tray. The inner Styrofoam cut is reusable for continued daily radiation treatment of the same patient for whom it was made until another custom field shaping is needed. In preparation to treat another patient, this cycle of block making is repeated.

However, the beam's intensity modulation by simpler means other than MLC is also made as an option in this invention. For this purpose, a Lucite plate with sliding lead sheets is placed on top of the custom shaped field forming inner Styrofoam cut. Through its slots, 0.637×2 mm sized lead or tungsten blades can be pushed inwardly or outwardly. A bade of 0.637 mm projects 1 cm at 100 cm source to skin distance (SSD or source to axis distance, (SAD). Multiple layers of such small lead or tungsten blades are attached to each of these slots. They are stacked on top of each other. They are placed on top of a 0.5 mm sized Lucite cm distance scalar. Based upon the desired intensity modulation, the number of such blades moved into the path of the beam is determined. Two mm thick lead reduces about 10% transmission of 6 MV photons and 8% transmission of 10 MV photons. Four mm thick lead reduces about 18% transmission of 6 MV photons and 15% transmission of 10 MV photons. Likewise, 6 mm thick lead reduces about 25% transmission of 6 MV photons and 22% transmission of 10 MV photons. There are 24 such beam intensity modulating stacked blades on each lateral side. The beam's intensity and shape is modulated by the number of blades inserted in the path of the beam and its distance from the periphery of the filed towards its center. With 24 such sliding stacks of beam intensity modulating lead or tungsten blades, any field's beam intensity can be modulated. Alternatively a simple lead cut with desired thickness placed on tope of the central block forming Styrofoam cut is sufficient for the desired beam's intensity modulation. Both these methods of beam's intensity modulation are simple and much more complex MLCs. They are easy to make and reuse until the end of a patient's IMRT treatment.

Beam's Intensity Modulation

In this invention, the intensity modulated IMRT is by means of multiple accelerators with varying energies all mounted on to the same gantry and all working together for simultaneous radiation to the tumor from multiple fields. Furthermore, within the custom shaped larger treatment filed, dynamic variable smaller field size adjusting movements of the secondary collimators is made to make multiple smaller fields. It is combined with selective dose rate and energy adjustments of the accelerator. This provides intensity modulated radiation therapy to the tumor without added scattered and leakage radiation as with IMRT with MLC. In effect, it is a single field treatment. The monitor units needed to treat the whole field is the same as in conventional radiation therapy. Hence it reduces the monitor units needed to treat a filed as compared to the segmented, static multiple small fields within a larger filed treatment with MLC. It also differs from the intensity modulating percent filtration of the beam as with dynamic beam delivery with MLC. Thus this field adjusting dynamic movement of the secondary collimator combined with dose rate and energy adjustments of the accelerator allows treating the tumor with lesser monitor units as compared to doing so with the MLC. Hence it generates lesser scatter and leakage radiation as compared to IMRT with MLC. The intensity of the radiation to a selected field is also modulated by selection of desired dose rates from each of the accelerators.

The dose rate and energy of each of these accelerators are selected as needed for the intensity modulation. Additionally, the treating field size is varied for each accelerator's to suit the beam's intensity modulated treatment volume that would represent the planning treatment volume, (PTV) or clinical treatment volume (CTV) or gross tumor volume (GTV). After treatment of a patient, the block forming cup and the Styrofoam inner cut are removed from the block forming tray. The inner Styrofoam cut is reusable for continued daily radiation treatment of the same patient for whom it was made until another custom field shaping is needed. In preparation to treat another patient, this cycle of block making is repeated.

Optional Intensity Modulation with Sliding Lead or Tungsten Blades

However, the beam's intensity modulation by simpler means other than MLC is also made as an option in this invention. For this purpose, a Lucite plate with sliding lead sheets is placed on top of the custom shaped field forming inner Styrofoam cut. Through its slots, 0.637×2 mm sized lead or tungsten blades can be pushed inwardly or outwardly. A bade of 0.637 mm projects 1 cm at 100 cm SSD or SAD. Multiple layers of such small lead or tungsten blades are attached to each of these slots. They are stacked on top of each other. They are placed on top of a 0.5 mm sized Lucite cm distance scalar. Based upon the desired intensity modulation, the number of such blades moved into the path of the beam is determined. Two mm thick lead reduces about 10% transmission of 6 MV photons and 8% transmission of 10 MV photons. Four mm thick lead reduces about 18% transmission of 6 MV photons and 15% transmission of 10 MV photons. Likewise, 6 mm thick lead reduces about 25% transmission of 6 MV photons and 22% transmission of 10 MV photons. There are 24 such beam intensity modulating stacked blades on each lateral side. The beam's intensity and shape is modulated by the number of blades inserted in the path of the beam and its distance from the periphery of the filed towards its center. With 24 such sliding stacks of beam intensity modulating lead or tungsten blades, any field's beam intensity can be modulated. Alternatively a simple lead cut with desired thickness placed on tope of the central block forming Styrofoam cut is sufficient for the desired beam's intensity modulation. Both these methods of beam's intensity modulation are simple and much more complex MLCs. They are easy to make and reuse until the end of a patient's IMRT treatment.

SUMMARY

In this AFS-IMRT system, multiple S-band, C-band or X-band microwave powered linear accelerators capable of delivering divergent therapeutic photon and electron beams are mounted on to a gantry with extensions to hold multiple accelerators are placed behind a KV-CT. The beam energies of each of these accelerators range from 4-15 MV. The gantry extensions to which each of these accelerators are mounted onto is made to rotate +−45°. The combined rotational capability of 4 accelerators each mounted on to separate gantry extensions is 360°. The gantry extensions to which the accelerators are attached to is moved forward or backward to treat a patient by SSD or SAD method. The capability to treat by SSD than by SAD method is to reduce the radiation to normal tissue.

In a modified version of this medical accelerator system, the bending magnet is eliminated to reduce the scattered radiation. In this instance, the accelerator is mounted on to the gantry extension as perpendicular to the target. This eliminates the need to use the 270° bending magnet used in most conventional medical accelerators. By eliminating this bending magnet, the scattered component of head leakage radiation is minimized. It reduces the total scattered radiation received by the normal tissue.

This divergent beam multi-accelerator system is equipped with semi automated Cerrobend or tungsten tertiary collimator. It differs much from the present conventional IMRT and IGRT systems including the TomoTherapy.

The TomoTherapy's IMRT with pencil beam is a segmented smaller field treatment within a larger field of treatment. Its transverse scan with narrow field thickness delivers higher monitor units which contributes high scattered and leakage radiation. Furthermore since many segments of treatment within a larger treatment field are to be completed, it is a slower treatment process. It reduces its radiobiological effectiveness. In contrast to AFSRT where the entire field is treated as a whole; not by dividing the field into multiple smaller segments as in Tomotherapy's slice by slice IMRT.

The present conventional IMRT and IGRT with a single accelerator unit and by multiple smaller field settings to treat a field within a beam's direction is an interrupted subfractionated radiation therapy system. The interrupted subfractionated radiation of 30-33 cGy per field to give total daily dose of 180-200 cGy is a protracted subfractionated daily radiation.

Delivering the total daily dose of radiation with multiple accelerators simultaneously eliminates the daily subfractionated radiation therapy. Hence, the dose rate at the tumor is increased to four times higher than when a tumor is treated by subfractionation. This increases the chances of inducing $\beta D_2$ like DNA breaks. Thus the AFSRT of a tumor with multiple accelerators could improve four to five fold tumor control probability. In brief, its radiobiological effects on lethal, sublethal and potentially lethal DNA damage and repair associated tumor cure with lesser toxicity to normal tissue is much higher.

Because of the simultaneous radiation to all the treatment fields and its higher dose rate effects, the total radiation dose to treat a tumor is reduced. In this instance, the dependence on isoeffective radiation dose on duration and number of fractionation, the time and radiation dose relationship has changed from all forms of present conventional daily fractionated radiation therapy including the 3-D conformal radiation therapy and the IMRT.

Most importantly, by treating all the fields simultaneously, the need for the patient to be placed in an uncomfortable position without any movements for a very long time to treat one filed after the other is eliminated. To place a sick patient on a hard treatment table and to except not to make any movements regardless of the patient's clinical condition and discomfort is an unusual physician's prescription due to its need and circumstances.

In those patients surviving longer after radiation therapy by IMRT, the risk to develop second malignancies is increased by 0.5% than when they are treated by 3-DCRT. It is due to a larger volume of normal tissue is radiated by conventional BART (C-IMRT). There is increased leakage and scattered radiation from increased monitor units used in C-IMRT. Due to beam modulation with MLC in C-IMRT, the ratio of monitor units used for C-IMRT vs conventional radiation therapy is increased by a factor of 2 to 4. It is estimated that it causes an additional 0.25% second malignancies in patients surviving longer after IMRT. Thus there is an increase of 0.75% second malignancies after IMRT. It is about twice the incidence of second malignancies observed with conventional radiation therapy (Hall, E. J. and Wuu, C. S. Radiation Induced Second Cancers: the Impact of 3D-CRT and IMRT, Int. J. Radiation Oncology, Biol. Phys., 56, p 83-88, 2003). This increased risk for second malignancies is reduced by 3-DC-AFS-IMRT with multiple accelerators and with semi automated tungsten powder mixture or melted Cerrobend blocks instead with conventional MLC.

3-DC-AFS-IMRT and IGRT with multiple accelerators operating in divergent beam mode synchronously and with melted Cerrobend or tungsten powder mixture tertiary collimator for custom filed shaping is combined with dynamic movements of the secondary collimators to create smaller fields within the larger treatment field for each beam's direction. It is combined with selective dose rate and energy adjustments of the accelerator. This provides intensity modulated beam delivery like in dynamic beam delivery with MLC; however it is with dynamic movements of the secondary collimators to make multiple smaller fields within the larger field of each beam directions. It does not involve partial absorption of the beam for intensity modulation. This provides a smoothly variable intensity profile as needed for the IMRT. In effect, it is a single field treatment and the monitor units needed to treat the whole field is the same as in conventional radiation therapy. Hence it reduces the monitor units needed to treat a filed as compared to the segmented, static multiple small fields within a larger filed treatment with MLC. It also differs from the intensity modulating percent filtration of the beam as with dynamic beam delivery with MLC. Thus this field adjusting dynamic movement of the secondary collimator combined with dose rate and energy adjustments of the accelerator allows treating the tumor with lesser monitor units as compared to doing so with the MLC. The intensity of the radiation to a selected field is also modulated by selection of desired dose rates from each of the accelerators.

This invention's AFSRT, and its 3-DC-AFS-IMRT and IGRT causes lesser scattered and leakage radiation. This combined with lesser MU usage makes it possible to treat a tumor with lesser radiation to normal tissue. Further more, this invention has the ability to treat a tumor by SSD than by the SAD method alone as in most IMRT systems including the TomoTherapy. It further reduces the radiation dose to normal tissue by about 3%. The SAD method of treatment by tomotherapy and the conventional IMRT has the disadvantage of increasing the normal tissue dose by 3%. This is in addition to the increased scattered and leakage radiation from higher MU usage associated higher dose to normal tissue. This 3% reduction reduces the dose to normal tissue by 240 cGy when a tumor is treated to a total dose of 8,000 cGy. Since about 4 times more MU is used by treating a tumor by conventional IMRT by SAD method, the dose to normal tissue could reach to about 1,200 cGy. It is about 12% higher doses to normal tissue for SAD method of treatment than for SSD method of treatment. Also radiation transmission through leave's rounded ends and the scatter and leakage radiation can amount up to fifteen percent and higher for large highly modulated fields.

TomoTherapy operates with maximum field size of 5×5 cm. This larger field size of 5×5 cm increases the leakage radiation. When all the smaller amounts of leakage radiation from each segment of treatment by Tomotherapy are summed together, there is a significant high dose of radiation to the normal tissue. Its leakage radiation increases proportionately with the field sizes from 0.5 cm to 2 and 5 cm. (2, Jeraj R et al, Radiation Characteristics of Helical Tomotherapy, Med. Phys. Vol. 31 (2), pp 396-404, 2004).

According to the International Electrical Commission (IEC) Standard 601-2-1, the leakage radiation for X-rays requires to be shielded to 0.6% of the central axis dose within the 40×40 cm maximum field size and to 0.1% over the reminder of a 2 meters circle of 2 meters radius in the patient plane at 60 cm from the X-ray source. The 5.7 MeV tomotherapy machine of TomoTherapy Inc. has 0.5% MLC infield leakage and 0.2% outside the field. (TomoTherapy Product Data Sheet) It is twice higher than the IEC standard of 0.1% leakage radiation for X-rays in a 2 meter circle radius in the patient plane at 60 cm from the X-ray source.

BRIEF DESCRIPTION OF THE DRAWINGS

FIGS. 3-A, 3-B-1, 3-B-2, 3-C-1 and 3-C-2 shows four medical accelerator combination of this invention with both SAD and SSD treatment capabilities.

FIGS. 6-1 to 6-6 illustrates the various aspects of a semi-automated tungsten powder mixture block (TPB) making device.

FIGS. 6-7 illustrates a semi-automated custom melted Cerrobend block making device FIG. 7 shows an optional beam's intensity modulating system with sliding lead blades.

REFERENCE NUMERALS

Figure 1:
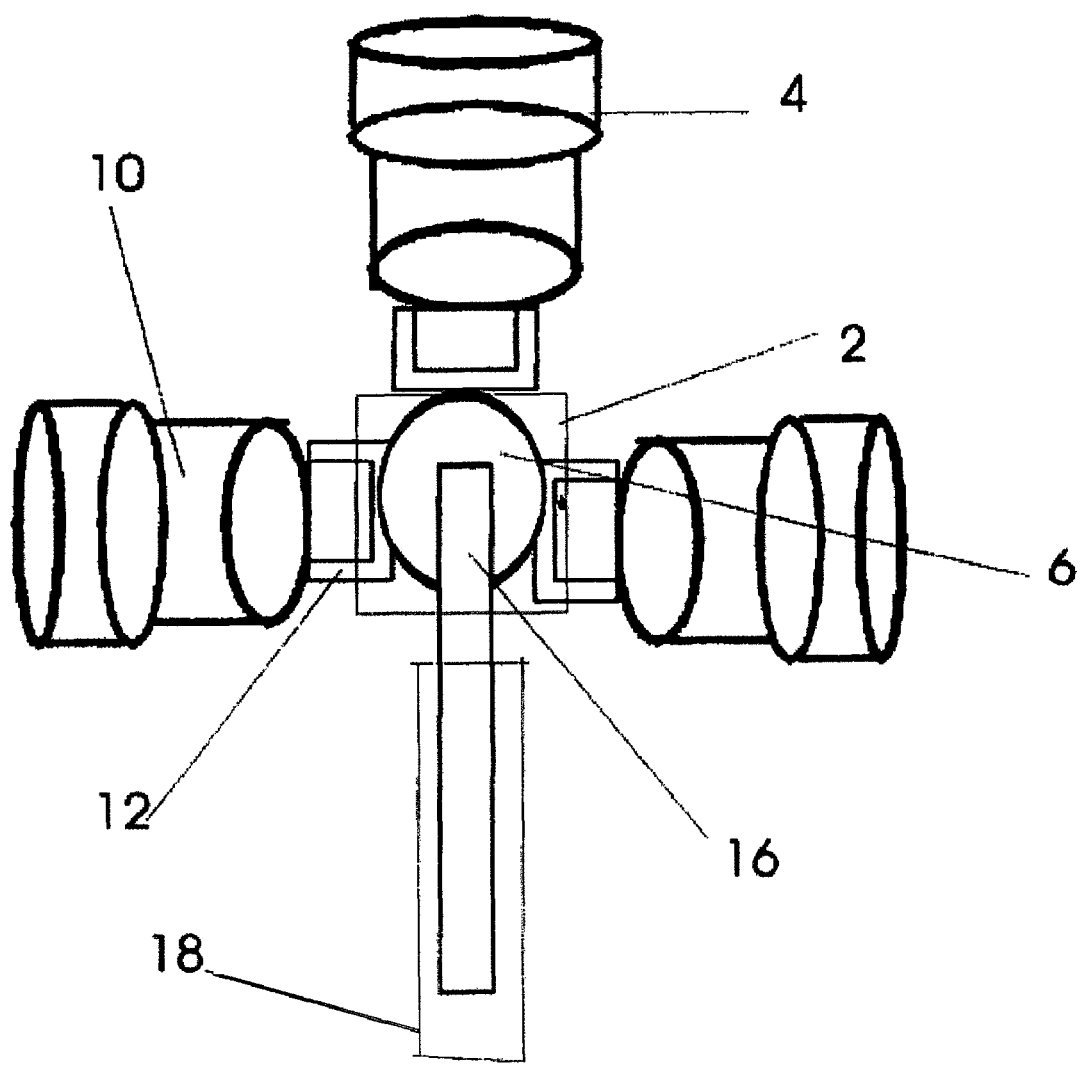
FIG. 1 illustrates a kV-CT combined with multiple accelerators for combined kV-CT and portal image guided treatment simulation, all field synchronous conventional radiation therapy, 3-D conformal all filed synchronous intensity modulated and image guided radiation therapy.

2 kV-CT
4 Medical accelerator
6 CT-gantry's opening
8 gantry of the medical linear accelerator
10 accelerator treatment head
12 accessory mount
14 accelerator holding gantry extension
16 flat tabletop insert
18 CT's table top
20 CT table's intermediate support
22 CT-table's base
24 CT-gantry
26 gyroscopes
27-1 electron gun
27-2 electron accelerating waveguide
27-3 bending magnet
27-4 secondary collimators
27-5 dose monitors
27-6 range finder
27-7 vacuum pump
27-8 injector system
27-9 RF system
27-9 injector system
27-10 auxiliary control chassis
27-11 field defining primary collimator
27-12 isocenter
28 gantry extending and retracting teethed bar
29 gantry rotation drive
30 teethed slots
32 fixed second bar
34 sliding bar's motor drive mechanism
36 engaging teeth and slot 38 bellowed connection of the gantry between its cut portions
40 microwave power source
42 microwave conducting tube
44 microwave power outlet openings
46 flexible microwave power transmission guides
48 tungsten powder holding bottom reservoir
50 tungsten powder block forming container
52 tungsten powder block
56 block holding tray
60 central Styrofoam cut
62 lateral Styrofoam cut
64 tungsten powder block forming container's four side walls
66 Lucite top cover plate of the tungsten powder block forming container
67 fixing nails
68 engaging slots in the sidewalls
70 centering cross hair lines
72 reticules
73 accessory holder slots 1 of the accessory holder
74 primary and secondary field shaping collimators
75 accessory holder slots 2 of the accessory holder
76 upper cover plate's boreholes
78 bottom cover plate of the tungsten powder block holding container
80 Styrofoam cuts holding Lucite tray
82 Lucite plate mount with 3 cm outwardly projecting edges
84 centering Lucite nails on Styrofoam cut holding Lucite tray
86 openings in the bottom cover plate of the tungsten powder block forming container
88 openings in the block holding tray of the accessory mount
90 openings in the tungsten powder holding bottom reservoir's upper cover
92 tightly fitting elastic plastic tubes
94 tightly fitting rubber seals with central openings
96 aligned interconnecting openings
98 tungsten powder holding bottom reservoir's top cover plate
100 Styrofoam block
102 mid Styrofoam cut
104 space occupied by the mid Styrofoam cut
108 Styrofoam cuts transferring Lucite plate with no openings
114 tungsten powder moving Lucite plate
116 length adjusting rods
118 volume adjusting ring
120 bellowed container
122 string and pulley
124 motor attached to the string and pulley
126 tungsten powder volume adjusting sensors
128 sensors placed at the top of the tungsten powder holding bottom reservoir
130 melted Cerrobend block-forming device
134 heating coils
136 beam filtering, sliding thin lead blades
138 distance adjusting scalar
140 custom shaped field

DESCRIPTION OF THE PREFERRED EMBODIMENTS

FIG. 1 illustrates a kV-CT 2 combined with multiple conventional divergent beam medical accelerator 4 for Combined kV-CT and portal image guided treatment simulation, all field synchronous conventional radiation therapy, 3-D conformal all filed synchronous intensity modulated and image guided radiation therapy. In this illustration, only the CT-gantry's opening for patient's positioning for CT-scan 6 is shown. The multiple medical accelerators attached to a single gantry are placed just behind the CT-gantry's opening 6 for patient's positioning for CT-scan. To show the accelerators placed behind the kV CT 2 the drawings of the rest of the CT-gantry is removed from this illustration. The medical accelerator 4 is attached to the gantry of the medical linear accelerator 8. The medical accelerator 4 with accelerator treatment head 10 and accessory mount 12 are attached to the gantry of the medical linear accelerator 8 by means of accelerator holding gantry extensions 14 (not visible in this illustration). The flat tabletop insert 16 is placed on the CT's table top 18. The flat table top insert 16 is used to place a patient for CT imaging and radiation therapy in treatment position and to eliminate the curvature of the CT's table top 18. The flat table top insert 16 on the CT's table top 18 is extended towards the CT-gantry's opening 6. By extending the CT's table top 18 with the flat table top insert 16 towards the CT gantry's opening 6, the CT table's intermediate support 20 is exposed. The CT table's intermediate support 20 rests on the CT-table's base 22 (not visible in this illustration).

Figure 2:
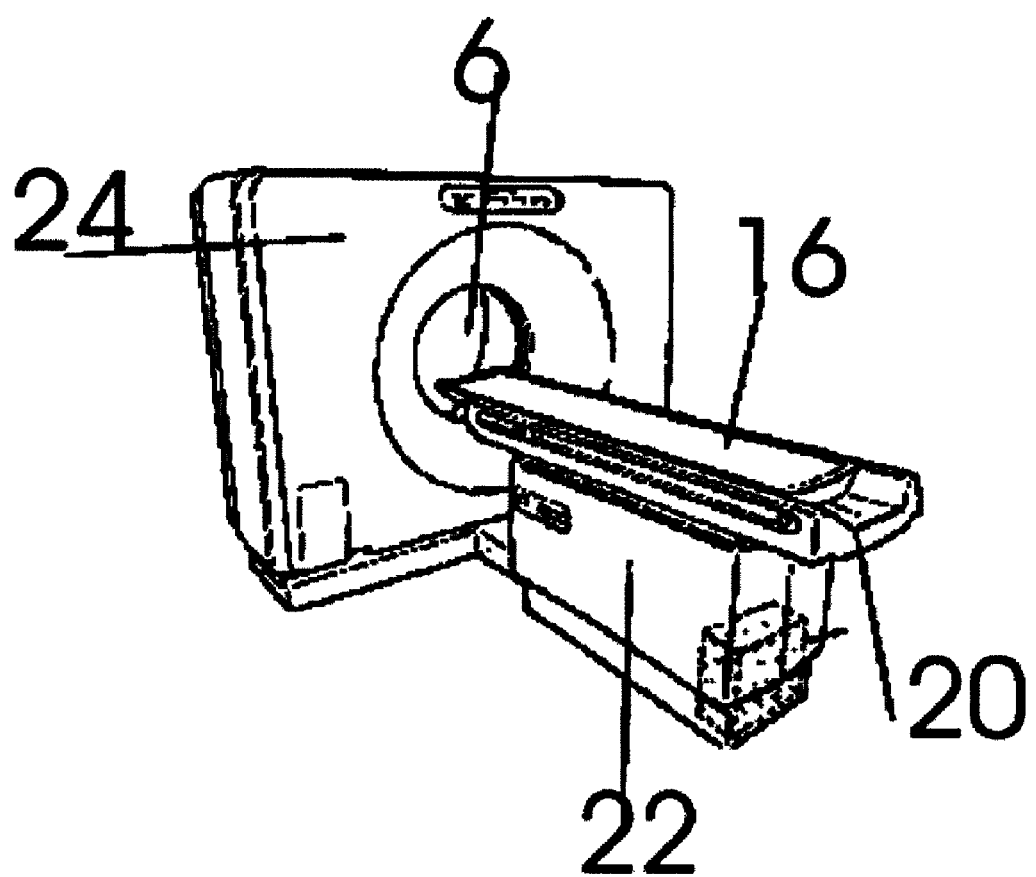
FIG. 2 illustrates a kV-CT that is placed in front of the gantry that holds multiple accelerators.

FIG. 2 illustrates a kV-CT that is placed in front of the accelerator. The CT-table's base 22, CT table's intermediate support 20, flat table top insert 16, CT-gantry's opening for patient's positioning for CT-scan 6, the CT-gantry 24 are shown in FIG. 2. To illustrate the accelerators behind the kV-CT, except for the CT-gantry's opening 6, the CT-gantry 24 was cutout in FIG. 1.

Figures 1, 6:
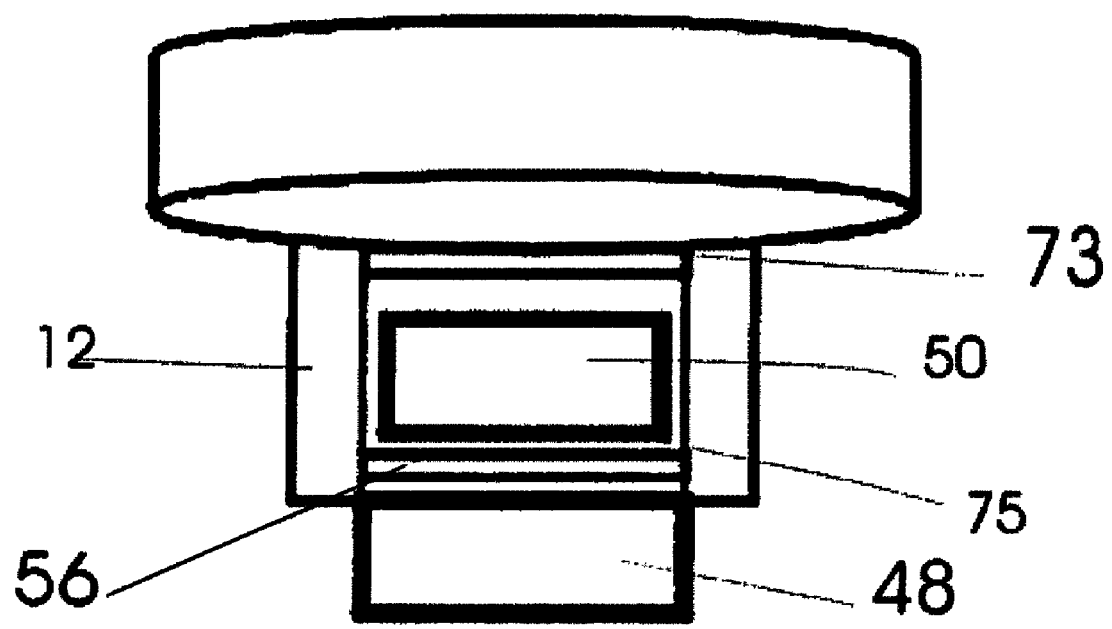
Figures 2, 6:
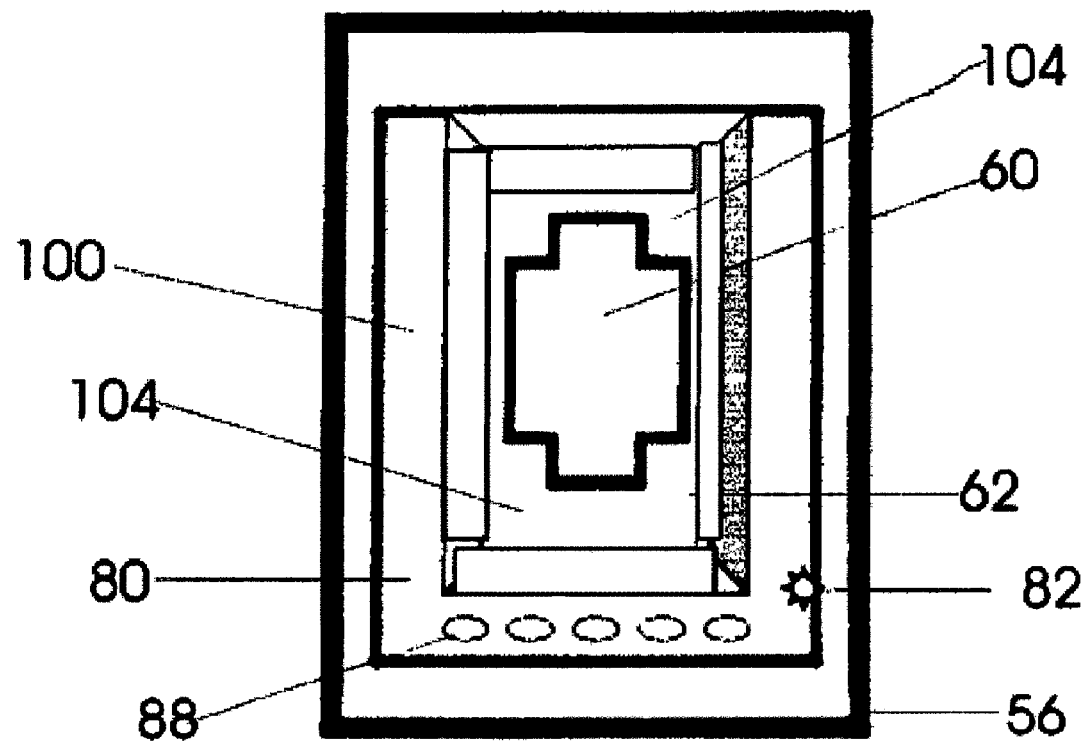
Figures 3, 6:
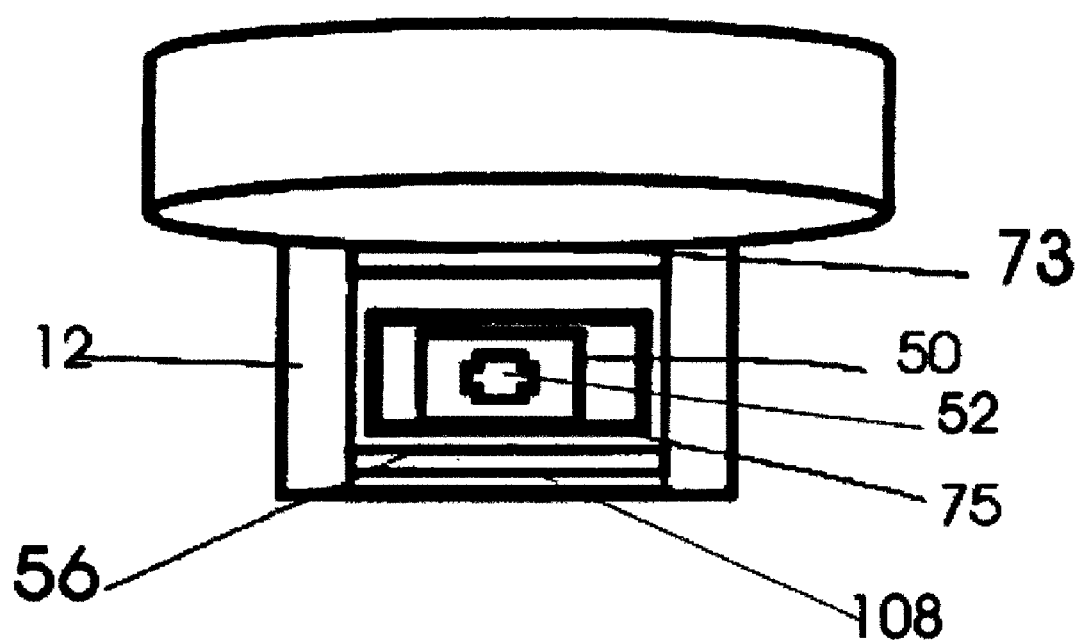
Figures 4, 6:
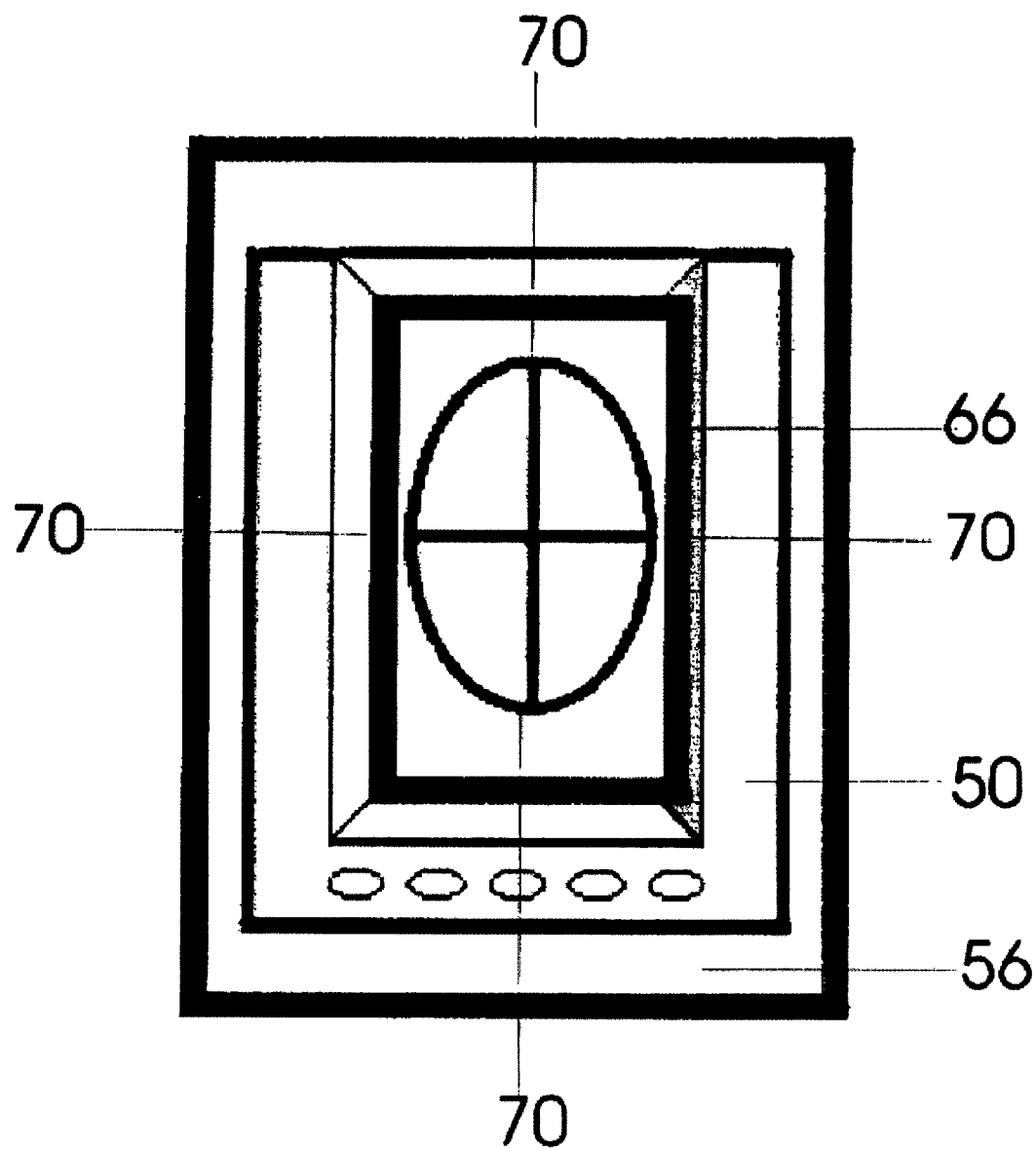
Figures 5, 6:
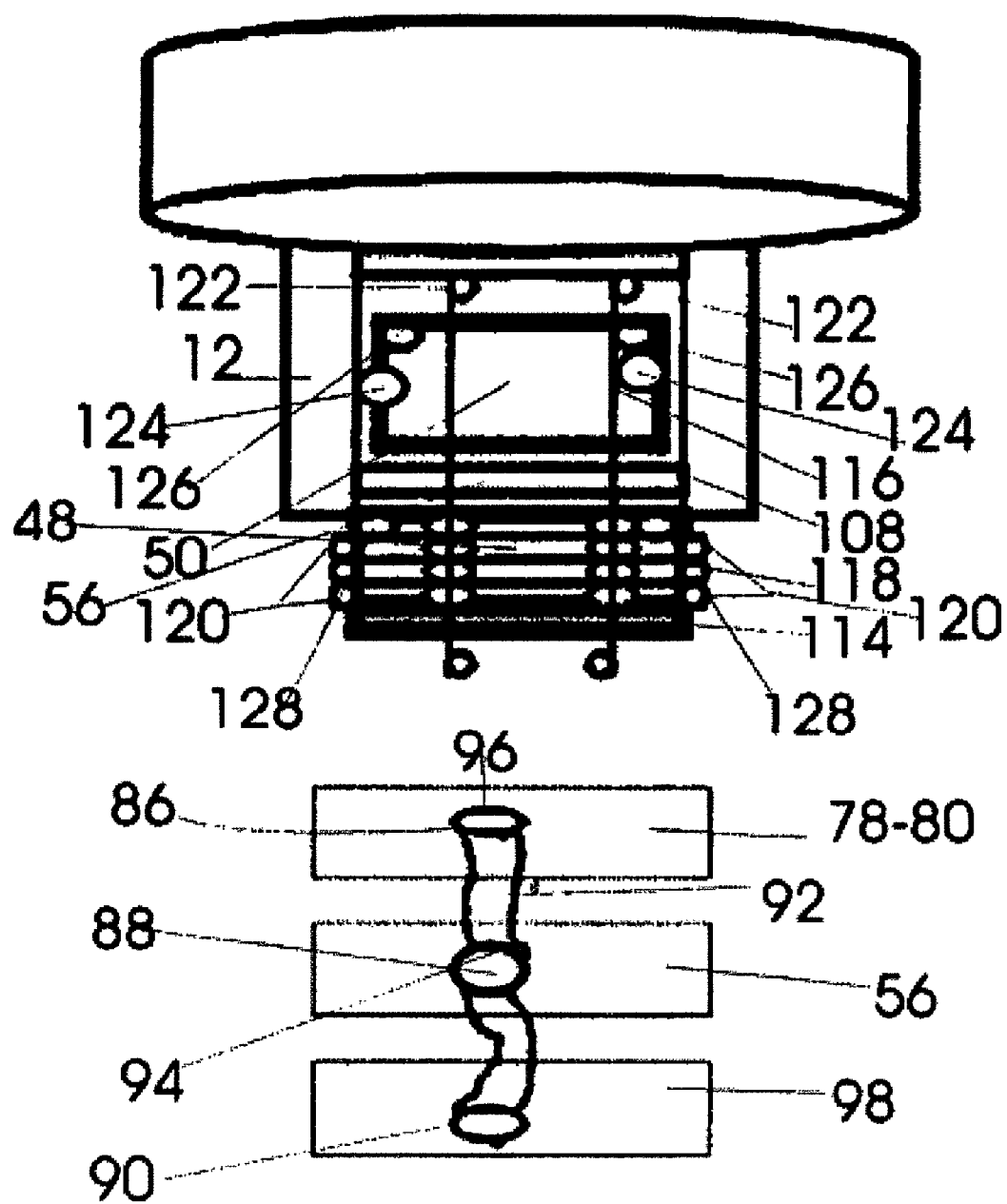
Figure 6:
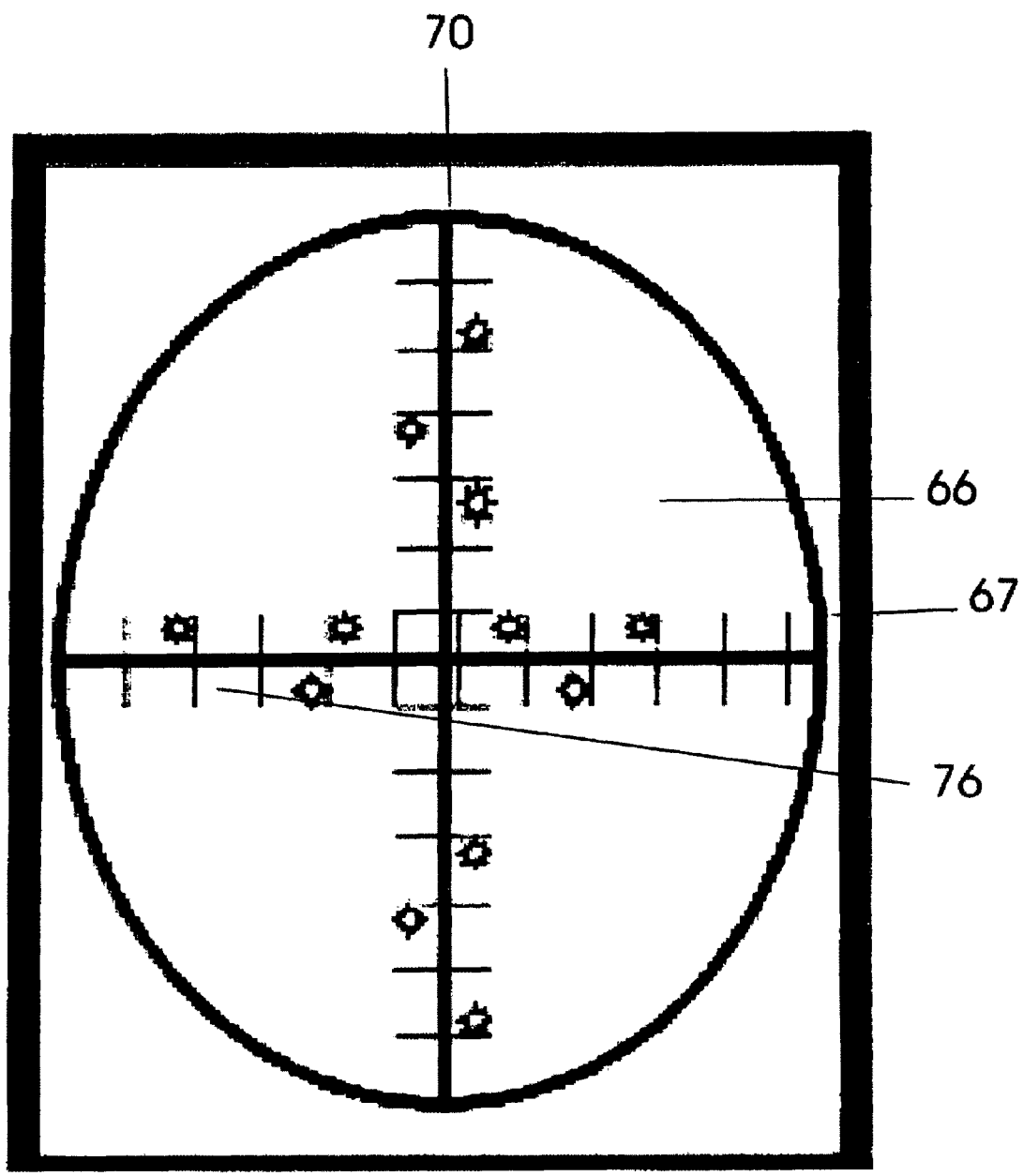

FIGS. 3-A, 3-b-1, 3-B-2, 3-C-2, and 3-C-2 shows four medical linear accelerator combinations of this invention and its major components. The accelerator combination is placed behind a kV CT 2. The major portion of the kV CT's gantry is not shown in this Figure. The kV CT 2 is in front of this multi-accelerator system. Hence it hides the front view of the multi-accelerator system. To illustrate the accelerator system, the kV CT 2 is removed from this FIG. 4-A.

FIG. 3-B-1 In this instance, the gantry with two accelerators attached at its both ends and the accelerator's rotational positions as at 0 and 180 degrees are illustrated. In FIG. 3-B-2 a second gantry with two accelerators also attached at its both ends and the accelerator's rotational positions as at 90 and 270 degrees are shown. Thus there are two main rotating gantries. Each of these gantries of the medical linear accelerators 8 holds two medical accelerators 4, one at each ends. These gantries are made to rotate around the CT's table top 18 with flat table top insert 16 when they are extended towards the accelerator system through the CT-gantry's opening as shown in FIG. 1. The accelerator treatment head 10 and accessory mount 12. The field size and gantry angle indicating gyroscope 26 is in the mid section of the gantry. The accelerator components including the electron gun 27-1, electron accelerating waveguide 27-2, bending magnet 27-3, field defining primary collimator 27-11 and secondary collimators 27-4, dose monitors 27-5, range finder 27-6, vacuum pump 27-7, injector system 27-8, RF system 27-9 including the RF power load and RF window, microwave source connection from magnetron or klystron 46, the injector system the accessory mount 12 that holds the custom shaped blocks, the modulator, the thyrotron, the power supplies, control cards, the water cooling system, the air pump and the auxiliary control chassis 27-10 all are the same as in a conventional medical linear accelerator.

The conventional accelerator's gantry rotation drive 29 is either duplicated or equipped with a clutch that selectively rotates each of the gantries. The rotation axis of the gantry and the collimator axis are made to intersect at 100 cm SSD. It is the intersecting isocenter 27-12 for the gantry and the collimator rotation. It is an adaptation of the conventional medical linear accelerator into a multi-medical linear accelerator system for simultaneous treatment of all the treatment fields at one time to avoid interrupted subfractionated daily fractionated radiation therapy.

FIG. 3-C-1 and FIG. 3-C-2 show the second gantry with another two accelerators. The accelerators 4 are attached at both ends and the gantry 8. In FIG. 3-C-1 the accelerators are shown at 0 and 180 positions. In FIG. 3-C-2 the accelerators are shown as at 90 and 360 degrees. The difference between FIG. 3-B-1 and FIG. 3-B-2 is that in this instance, accelerator extending and retracting teethed bars are incorporated into the gantry 8. To make extension or retraction of each accelerators, the parts of the accelerator that holds electron gun 27-1, accelerating wave guide 27-2, bending magnet, 27-3 treatment head 10, range finder 27-6, vacuum pump 27-7, RF system 27-9 and the dose chamber 27-5 of each accelerator is made to slide on a gantry extending and retracting teethed bar 28 that engage with the teethed slots 30 in a fixed second bar 32. These accelerator extending and retracting bars are incorporated within the gantry. Like in a conventional medical accelerator, both gantries and the accelerators are isocentrically mounted. However in this instance, they have the capability to extend or retract individually to plus or minus 20 cm to make adjustments for the selection of SSD or SAD method of treatments. When the accelerators are in isocentric position, SAD and rotational methods of treatments are possible. The sliding bar is driven forward or backward by the sliding bar's motor drive mechanism 34. It drives the sliding gantry extending and retracting teethed bar 28 on the fixed second bar 32. This facilitates the extension and retraction of the accelerators at both ends of the gantry. Without the gantry's extension or retraction the accelerator treatment head is at isocenter distance of 100 cm. In this isocentric position, the SAD method of treatment is feasible. When the accelerator with the treatment heads are moved to adjust the SSD, the SSD method of treatment is feasible. Forward or backward movement of one of the engaging teeth and slot 36 on these bars moves the accelerator and the treatment head 1 cm forward or backward. The maximum forward or backward travel distance of the sliding teethed bar on the fixed second bar 32 is limited to 20 cm. A 20 cm forward extension or 20 cm backward retraction of the sliding gantry extending and retracting teethed bar 28 increases the SSD to 120 cm or decreases to SSD to 80 cm. If a lesser forward or backward extension or retraction is elected then these SSD distances is adjusted accordingly. A bellowed connection of the gantry between its cut portions 38 facilitates these extending and retracting movements of the accelerator 10 with the accessory mount 12. To maintain the treatment position of the patient placed on the CT's table top 18 with the flat table top insert 16, after the kV CT imaging for IGRT is done no additional CT-table positional changes are made during the radiation therapy with these multiple accelerator system of this invention.

Figure 4:
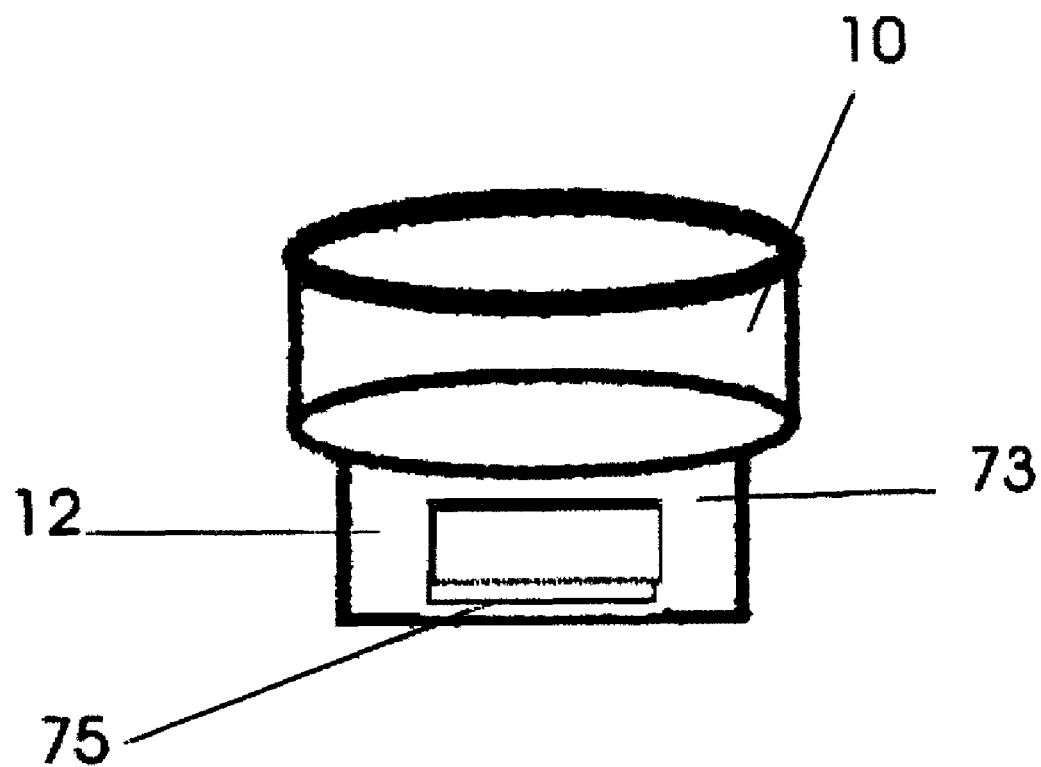
FIG. 4 is an illustration of the medical linear accelerator's treatment head and accessory holding double gantries.

FIG. 4 is an illustration of a conventional medical linear accelerator's treatment head 10 and accessory Mount 12. The reticule 72 is inserted to the accessory holder slot 1 of the accessory holder 73. The block holding tray 56 is inserted to the accessory holder slot 2 of the accessory holder 75. The accessory holder 12 is modified as part of the custom field shaping device with tungsten powder or with melted Cerrobend.

Figure 5:
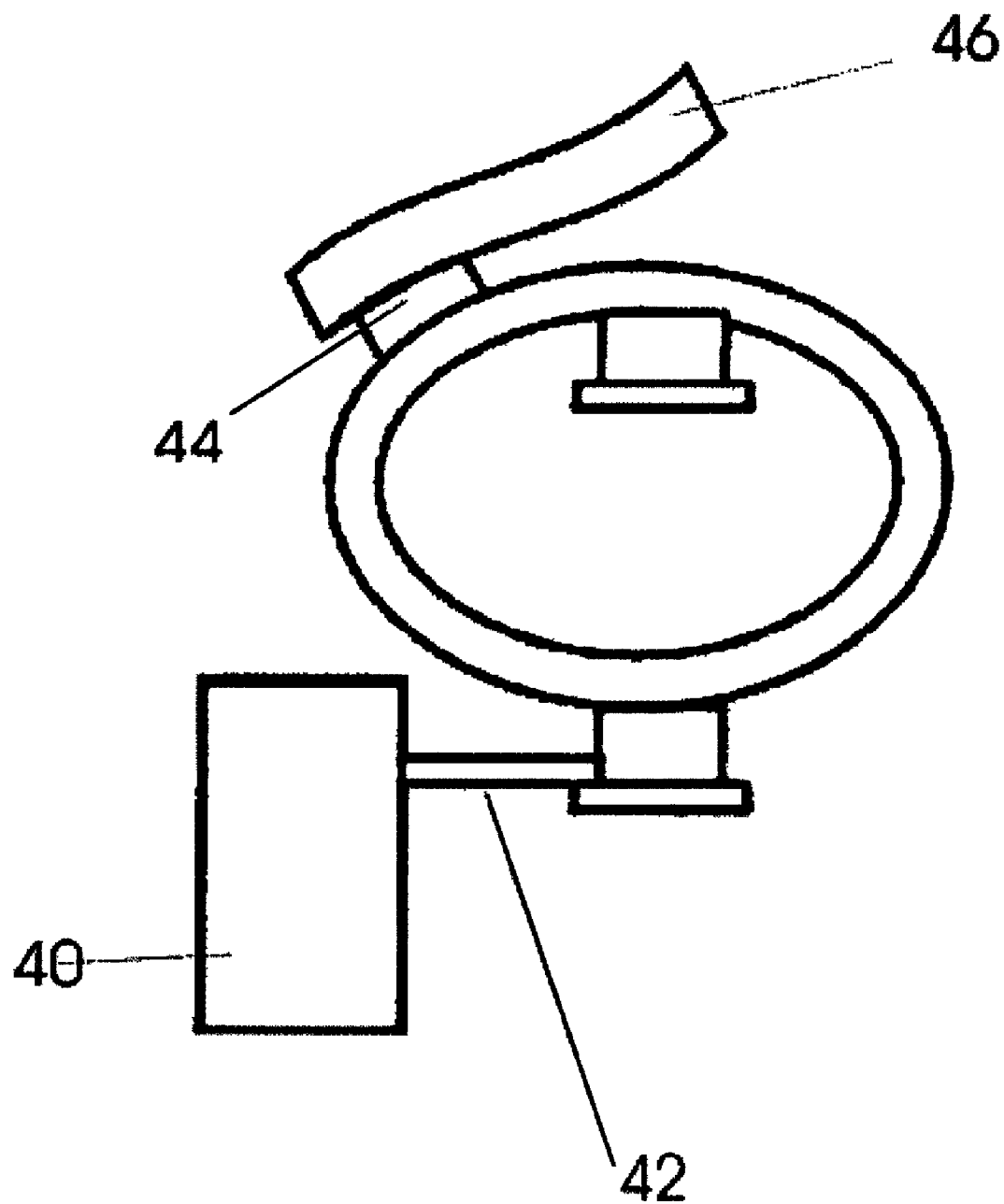
FIG. 5 illustrates the microwave power source

FIG. 5 illustrates the microwave power source. The microwave power source 40 is a magnetron or a klystron. From the microwave power source 40 microwaves is transmitted into a circular microwave conducting tube 42 with microwave power outlet openings 44. From the microwave conducting tube 42 microwave power is extracted through its microwave power outlet openings 44 and it is conducted to each accelerator through flexible microwave power transmission guides 46.

FIG. 6-1 to 6-6 illustrates the various aspects of a semi-automated tungsten powder mixture block (TPB) making device. The tungsten powder is easily dispensable into any container. By applying modest pressure, it is easily pushed from an interconnecting tungsten powder holding bottom reservoir 48 into a tungsten powder block forming container 50 that also serves as the upper tungsten powder holding upper reservoir FIG. 6-1. The tungsten powder block 52, FIG. 6-3 is formed within the space occupied by the mid Styrofoam cut 104, FIG. 6-2. The block forming Styrofoam cuts, the central Styrofoam cut 60 and the lateral Styrofoam cut 62 are placed on to the Styrofoam cut holding Lucite tray 80, FIG. 6-2 is inserted into a tungsten powder block forming container 50 held at the top of the block holding tray 56 of the accessory mount 12. The tungsten powder block-forming container 50, FIG. 6-3 is shaped to hold the block forming Styrofoam central cut 60 and the Styrofoam lateral cut 62 like the one used to make custom Cerrobend block for radiation therapy. In this instance, the central Styrofoam cut 60 and lateral Styrofoam cut 62 are used to shape the custom tungsten powder block 52 with tungsten powder. A container is made to hold the Styrofoam cuts on top of the block holding tray. This tungsten powder block forming container 50, FIG. 6-3 is a 20.5×20.5×8 cm sized square container that holds the central Styrofoam cut 60 and lateral Styrofoam cut 62 and tungsten powder block 52. The tungsten powder block forming container's four side walls 64 is equipped to hold a Lucite top cover plate 66, FIG. 6-4 and FIG. 6-6. All three sides at the top of these sidewalls are equipped with engaging slots. These engaging slots in the sidewalls 68 is to slide in a 20×20×0.5 cm thick Lucite top cover plate of the tungsten powder block forming container 66 from its remaining open side. This Lucite top cover plate of the tungsten powder block forming container 66 is marked with centering cross hair lines 70 that are in alignment with the cross hair makings of the reticule 72 that is placed below the primary and secondary field shaping collimators 74. These centering lines are used for nailing centered additional support onto central Styrofoam cut 60 and lateral Styrofoam cut 62 beneath the Lucite top cover plate of the tungsten powder block forming container 66. Through the upper cover plate's boreholes 76, FIG. 6-6 that are drilled on top of the Lucite top cover plate of the tungsten powder block forming container 66, fixing nails 67, FIG. 6-6 made of Lucite are inserted to hold the central Styrofoam cut 60 and lateral Styrofoam cut 62 firmly after they are inserted into the tungsten powder block forming container 50 along the centering lines marked on the Styrofoam cuts. The bottom cover plate of the tungsten powder block holding container 78 FIG. 6-5 is formed by a 20×20×0.5 cm Lucite plate when it is inserted with the block forming central Styrofoam cut 60 and lateral Styrofoam cut 62. Before inserting the central Styrofoam cut 60 and lateral Styrofoam cut 62 into the tungsten block forming container 50, they are fitted on to this 20×20×0.5 cm Styrofoam cuts holding Lucite tray 80 as centered to the central axis and to the divergence of the radiating beam. The tungsten powder block forming container 50 is mounted on to a 5×27.5×0.5 cm Lucite plate mount with 3 cm outwardly projecting edges 82. Several boreholes are drilled onto the outwardly projecting portion of this bottom Lucite mount. Through corresponding boreholes drilled onto the block holding tray 56, FIG. 6-1, FIG. 6-2 of the accessory mount 12, the tungsten powder block holding container 50 is fixed on to the block holding tray 56 with Lucite nuts and bolts. It is not removed from the block holding tray 56 during the process of tungsten powder block makings. Cross hair lines centering with the central axis and divergence of the beam are marked on top of the block holding tray 56 of the accessory mount 12. It is marked as in alignment with the cross hair makings of the reticule 72 that is placed below the primary and secondary field shaping collimators 74. These centering cross hair lines 70, FIG. 6-4 and FIG. 6-6 are used for placement of the tungsten powder block forming Styrofoam cuts into the tungsten powder block forming container 50. It is also fixed on top of the block holding tray 56 of the accessory mount 12 as centered with the central axis and the divergence of the radiating beam. Styrofoam cuts holding Lucite tray 80 is fitted with 5 cm long centering Lucite nails along the centering lines of the divergent radiating beam. These centering Lucite nails on Styrofoam cut holding Lucite tray 84 are used to fix the Styrofoam cuts firmly onto the Styrofoam cut holding Lucite tray 80. Before inserting the block forming central Styrofoam cut 60 and lateral Styrofoam cut 62 into the tungsten powder block forming container 50, they are fixed on to the Styrofoam cuts holding Lucite tray 80 as centered to the central axis and the divergence of the radiating beam with the aid of the centering lines as projected from the reticule 72. These lines are etched onto this Lucite plate. When this Styrofoam cuts holding Lucite tray 80 with the Styrofoam cuts as fixed onto it is inserted into the tungsten powder block forming container 50, this Lucite tray also becomes the bottom cover of the tungsten powder block forming container. Inlet-outlet openings are drilled on to the Styrofoam cuts holding Lucite trays 78-80, onto the block holding tray 56 of the accessory mount 12 and on top cover of the tungsten powder holding bottom reservoir's Lucite plate 98, FIG. 6-5. They function as interconnecting openings for moving the tungsten powder into the tungsten powder block forming container on top of the block holding tray or into the tungsten powder holding bottom reservoir below the block holding tray.

The openings in the bottom cover plate of the tungsten powder block forming container 86, the openings in the block holding tray of the accessory mount 88 and the openings in the tungsten powder holding bottom reservoir's upper cover 90 are interconnected with tightly fitting elastic plastic tubes 92, FIG. 6-5. The top portion of the openings in the block holding tray 88 of the accessory mount 58 are fitted with tightly fitting rubber seals with central openings 94, FIG. 6-5. These rubber seals projects 0.5 cm upwards from the top of the block holding tray 56 of the accessory mount 12. The bottom cover plate of the tungsten powder block holding container 78 with the tungsten powder block forming central Styrofoam cut 60 and lateral Styrofoam cut 62 is inserted into the tungsten powder block forming container 50 as aligned with these rubber seals with central openings 94. With these openings centered and tightly secured on top of the block holding tray 56 of the accessory holder 12, aligned interconnecting openings 96, FIG. 6-5 are established between the tungsten powder block forming container 50, block holding tray 56 of the accessory mount 12 and the tungsten powder holding bottom reservoir's top cover plate 98. The tightly fitting rubber seals with central openings 94 at the top of the block holding tray 56 of the accessory mount 12 prevent any leakage of the tungsten powder during its passage to and from the tungsten powder block forming container 50.

A 20×20×7.5 cm sized Styrofoam block 100 can be tightly fitted in to the tungsten powder block forming container 50. Styrofoam cuts are made similar to the custom Cerrobend block making Styrofoam cuts from a standard 20×20×7.5 cm sized Styrofoam block 100 with the aid of a Styrofoam cutter like the Huestis Styrofoam cutter or by computer controlled automated custom field shaping Styrofoam cutters. To make the tungsten powder block, the mid Styrofoam cut 102 is removed and the space occupied by the mid Styrofoam cut 104 is filled with tungsten powder, FIG. 6-2.

To fill the space occupied by the mid Styrofoam cut 104 semi-automatically, first the central Styrofoam cut 60 and lateral Styrofoam cut 62 are fitted on top of the bottom cover plate of the tungsten powder block holding container 78 as centered to the central axis of the divergent beam with the aid of the centering cross hair markers etched onto it. This Lucite plate with the Styrofoam cuts is then placed on to another 20×20×0.5 cm sized Styrofoam transferring Lucite plate with no openings 108 drilled onto it. After removing the Lucite top cover plate of the tungsten powder block forming container 66, it is inserted into the tungsten powder block forming container 50. Afterwards the Styrofoam cuts transferring Lucite plate with no openings 108, FIG. 6-3 is pulled out of the tungsten powder block forming container. It opens the openings in the bottom cover plate of the tungsten powder block forming container 86. Those openings are now in continuity with the openings in the block holding tray of the accessory mount 88 and with the openings in the tungsten powder holding bottom reservoir's upper cover 90. Tungsten powder block is formed within the space occupied by the mid Styrofoam cut 104, FIG. 6-2 when, the tungsten powder from the tungsten powder holding bottom reservoir 48 is pushed onto it by inserting pressure on to the tungsten powder holding bottom reservoir 48. The tungsten powder block 52 is shaped for its conformity with the divergence of the radiating beam. The block forming Styrofoam cuts are cut in conformity with the slope of the diverging radiating beam. It provides a slanting downward slope according to the beam divergence. When the pressure on the tungsten powder holding bottom reservoir 48 is released, the flow of the tungsten powder is reversed; in this instance, by gravity the tungsten powder 106 from the tungsten powder block forming space occupied by the mid Styrofoam cut 104 in the tungsten powder block forming container 50 drops back into the tungsten powder holding bottom reservoir 48 through the interconnecting openings in this block forming device, openings in the bottom cover plate of the tungsten powder block forming container 86, openings in the block holding tray of the accessory mount 88 and with the openings in the tungsten powder holding bottom reservoir's upper cover 90, FIG. 6-5. When the Styrofoam cut is empty from the tungsten powder, the Styrofoam cuts transferring Lucite plate with no openings 108 is reinserted back to its place, at the bottom of the bottom cover plate of the tungsten powder block holding container 78 which has connecting openings for connection with other block forming compartments as described above. Then the bottom cover plate of the tungsten powder block forming container 86 and the Styrofoam cuts transferring Lucite plate with no openings 108 are pulled out of the Styrofoam block forming container 50. This removes the Styrofoam cuts from the tungsten powder block forming container 50 without spillage of the tungsten powder 106.

On the block holding tray 56, twelve two and a half cm sized openings are drilled to allow passage of the tungsten powder upwards or downwards. They are drilled within the space that will represent the tungsten powder block forming space occupied by the mid Styrofoam cut 104. Such openings around the central Styrofoam cut gives 12 openings around the central Styrofoam cut 60. The central Styrofoam cut 60 is inserted as aligned to the centering cross hair lines etched on top of the bottom cover plate of the tungsten powder block holding container 78. The openings around the central Styrofoam cut are in alignment with openings in the bottom cover plate of the tungsten powder block forming container 86, openings in the block holding tray of the accessory mount 88 and with the openings in the tungsten powder holding bottom reservoir's upper cover 90, FIG. 6-5. Through these aligned openings, tungsten powder is pushed from the tungsten powder holding bottom reservoir 48 to the space occupied by the mid Styrofoam cut 104 in the tungsten powder block forming container 50 at the top of the block holding tray 56 of the accessory mount 12 until the space occupied by the mid Styrofoam cut 104 is filled with tungsten powder to form the custom shaped tungsten powder block within the space formerly occupied by the mid Styrofoam cut. After treating a patient with the aid of this custom shaped tungsten powder block within the space formerly occupied by the mid Styrofoam cut, the tungsten powder is removed from the tungsten powder block forming container 50 by gravity drop of the tungsten powder back into the tungsten powder holding bottom reservoir 48 by releasing the pressure to the tungsten powder holding bottom reservoir 48. This process of custom tungsten powder block making is repeated each time a new patient is setup for the treatment.

As described earlier, the central Styrofoam cut 60 is used to make the custom shaped tungsten powder block within the space formerly occupied by the mid Styrofoam cut 112. The central Styrofoam cut 60 is fixed on to the block forming tray 56 as centered to the projected cross hairs of the reticule. The center relative to the horizontal and the vertical dimension of the diverging beam at the top and bottom of the Styrofoam cut is marked. It is cut in conformity with the diverging beam. Using these horizontal and vertical lines marked at the bottom of the central Styrofoam cut, it is inserted on to the centering Lucite nails 84 on the block holding tray 56 as centered to the central axis of the beam and in conformity to the projected crosshairs of the reticule and divergence of the beam. It is thus centered and fixed on to the block holding tray.

The measurement of transmission of 6 and 10 MV radiation beam through the central Styrofoam cut so fixed onto the block holding tray shows only about less than 1% attenuation of 6 and 10 MV beams.

At the under surface of the accessory mount 12 of the accelerator's treatment head 10 tungsten powder holding bottom reservoirs 48 are attached. To keep them away from the diverging beam's path, they are made as a 10×25×10 cm sized elastic container. It extends to the under surface of the block holding tray 56 when it is inserted on to the accessory mount 58. There are 12, two and a half cm sized openings in mid Styrofoam cut region on the block holding tray. They are in coincidence with similar holes at the top of the block holding tray. These openings in the block holding tray of the accessory mount 88 connect with the upper tungsten powder block forming container 50 and the tungsten powder holding bottom reservoir 48. The bottom of the tungsten powder holding bottom reservoir 48 is mounted on top of a 10×25×1 cm tungsten powder moving Lucite plate 114. The outer ends of these plates are connected to the upper side of the block holding tray by means of 10 cm long 2 cm diameter connecting rods 116 that pass up or down through a volume adjusting ring 118. The top and bottom of this length adjusting rods 116 with fitted the volume adjusting ring 118 for connecting rod's 116 upward and downward travel. There is one such rod at each corner ends of this bottom reservoir holding tray. Its upper end is fitted onto the block holding tray 56 in similar way. This entire system of tungsten powder holding bottom reservoir 48 is enclosed in a bellowed container 120 that moves with this reservoir upwards or downwards based upon volume adjusting pressure inserted on it, FIG. 6-5.

Upwards or downwards hand or motor driven movements of all the four connecting rods 116 simultaneously pushes the elastic tungsten powder containing reservoir upwards or downwards. For hand driven upward or downward movement of these reservoirs, a string and pulley 122 attached to the bottom and upper reservoirs is pulled or released. For automatic filling and emptying of the tungsten powder holding reservoirs, a motor attached to the string and pulley 124 winds the string clockwise or anticlockwise. Consequently, its content, the tungsten powder is pushed upwards or downwards. When it is pushed upwards, the tungsten powder is pushed upwards into the tungsten powder block forming container 50 at the top of the block holding tray 56. The level of such filling with the tungsten powder into the block forming container is controlled by sensors that controls the revolution of the motor attached to the string and pulley 124. Such tungsten powder volume adjusting sensors 126 are attached to the under surface of the top of the tungsten powder block forming containers sidewalls 64. When the motor attached to the string and pulley 124 rotates counterclockwise the plate holding the lower reservoirs are pushed downwards. It expands the elastic lower reservoir and hence the tungsten powder drops into the lower reservoir. It empties the block forming container from the tungsten powder. When it is empty, and the tungsten powder holding bottom reservoir 48 is full, the sensors placed at the top of the tungsten powder holding bottom reservoir 128 sends signals to the motor to stop clockwise rotation of the motor attached to the string and pulley 124. When the hand driven mechanism is used, the sensors sends an alarm signal to stop pulling or releasing.

In summary, for custom block making to shape a treatment field, the tungsten powder block forming container is removed from the top side of the block holding tray and it is fitted with the central and lateral Styrofoam cuts as centered to the central axis of the diverging beam as described earlier. It is then tightly covered with the tungsten block forming container and inserted to the accelerator's accessory holder. For each patient, shaped block making Styrofoam cuts are made and fixed on to the block holding tray as above. By pushing the tungsten powder from the lower reservoir into the empty space in the Styrofoam cut in the tungsten powder block making container the semi automated tungsten powder block making is done. After treating a patient, the Styrofoam cut is emptied automatically and the block holding tray with the empty Styrofoam cut is removed. A patient's custom Styrofoam cut fixed on to the block holding tray is repeatedly used for the daily radiation treatment of that patient. For treating the next patient, that patient's block holding tray with the Styrofoam cut is inserted to the accelerator's accessory holder and the semi automated tungsten powder block making is repeated and the patient is treated. This process is repeated for the treatment of each patient. It is not a lengthy or tedious process. It has much lesser scatter, leakage and penumbra radiation than when MLCs are used for 3-DCRT and IMRT.

Figures 6, 7:
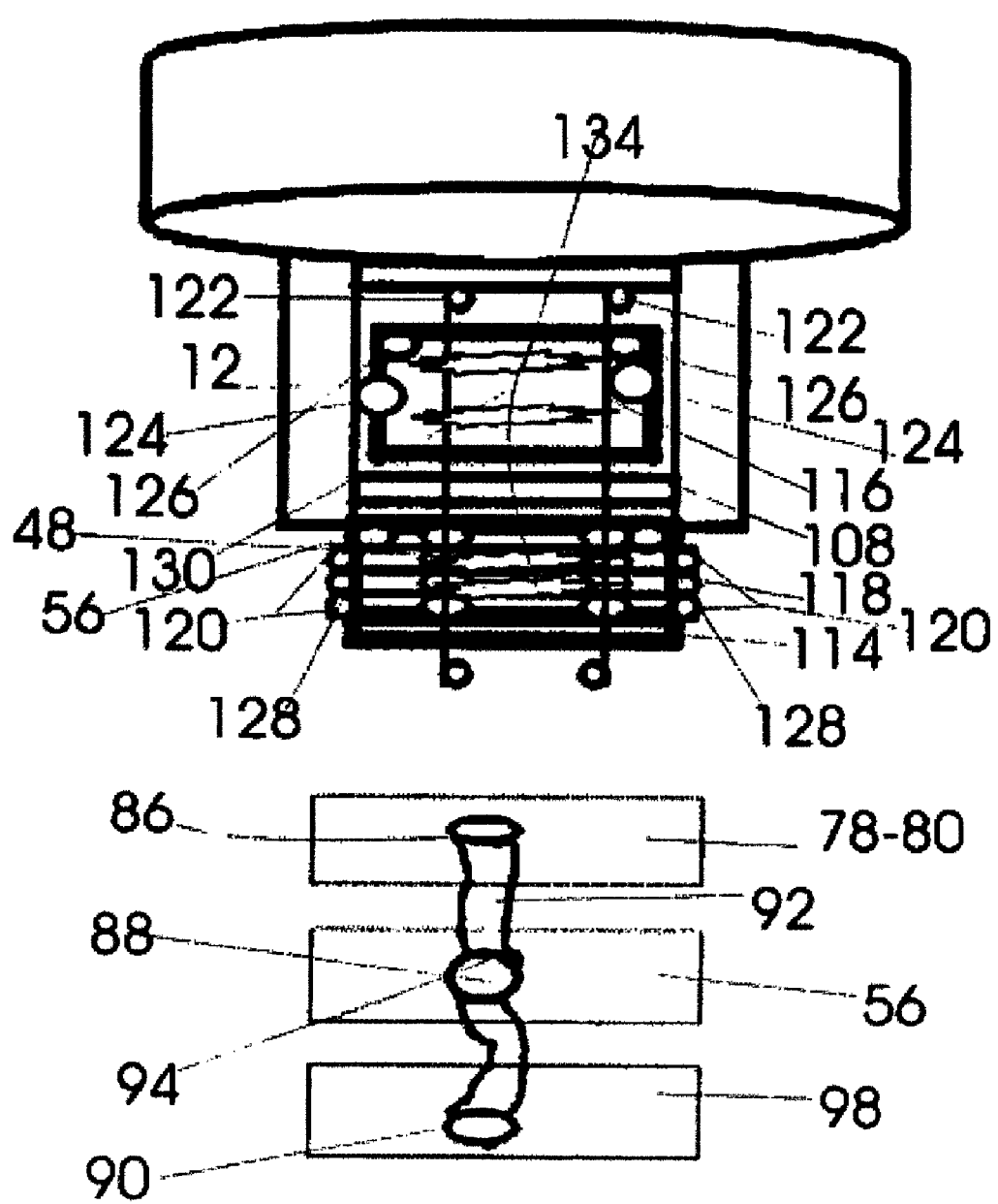
Figure 7:
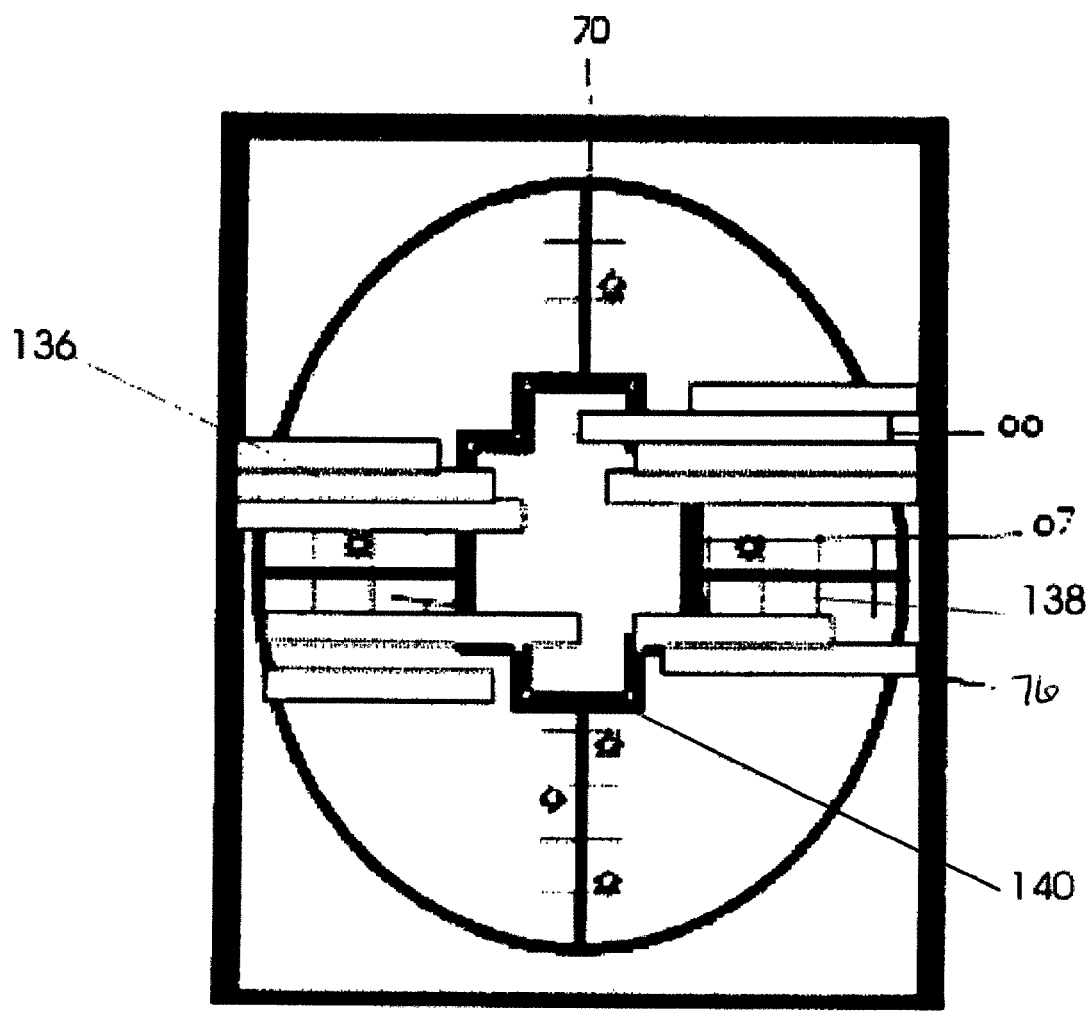

FIG. 6-7 illustrates a semi-automated custom melted Cerrobend block making device 130. In this instance, Cerrobend is heated to 70° C. with heating coils 134 to keep it as freely flowing melted Cerrobend (MC) form in reservoirs. From MC, custom shaped melted Cerrobend block (MCB) is made to custom shape the field for radiation. Each time when the patient is setup for radiation therapy, custom shaped MCB is made to shape the field of radiation. The tertiary block holding tray is modified to shape and hold the custom shaped MCB. Like by the tungsten powder custom block making, the Styrofoam cuts are made, the central Styrofoam cut 60 and the lateral Styrofoam cut 62 are fixed on to Styrofoam cut holding Lucite tray 80 with centering Lucite nails and the flow of melted Cerrobend upwards from the bottom reservoir to make the custom block and downwards from the upper reservoir to empty the upper reservoir is performed as in the case of tungsten powder block making.

FIG. 7 shows an optional beam's intensity modulating system with sliding lead blades. It is achieved with partial beam filtering sliding thin lead blades 136. They are selectively inserted in the path of the beam that radiates the PTV, CTV and the GTV. In this instance, the Lucite top cover plate of the tungsten powder block-forming container 66 is equipped with 24 slots at each lateral side. To each of these slots, 0.637 cm sized beam filtering sliding thin lead blades 136 are inserted. Each of these lead blades projects 1-cm sized partial block at 100-cm SSD or SAD. Multiple layers of such small lead blades are attached to each of these slots. They are stacked on top of each other and on tops the Lucite top cover plate of the tungsten powder block-forming container 66. Distance adjusting scalar 138 is attached to the Lucite top cover plate of the tungsten powder block-forming container 66. The scalar is marked at every 0.5-cm distance. The partial beam filtering sliding thin lead blades 136 is moved towards the radiation field encompassing the regions of PTV, CTV and GTV within the custom shaped field 140. Based upon the desired intensity modulation, the number of such blades moved into the path of the beam is determined. Two-mm thick lead reduces about 10% transmission of 6 MV photons and 8% transmission of 10 MV photons. Four-mm thick lead reduces about 18% transmission of 6 MV photons and 15% transmission of 10 MV photons. Likewise, 6-mm thick lead reduces about 25% transmission of 6 MV photons and 22% transmission of 10 MV photons. There are 24 such beam intensity modulating stacked blades on each lateral side. The beam's intensity and shape is modulated by the number of blades inserted in the path of the beam and its distance from the periphery of the filed towards its center, namely at PTV, CTV or GTV. With 24 such sliding stacks of beam partially filtering lead blades, any field's beam intensity can be partially modulated. For each patient, a set of partial beam filtering lead blades on the Lucite top cover plate of the tungsten powder block-forming container 66 is moved towards the PTV, CTV and GTV to achieve the desired intensity modulation. It is reused until the end of the entire course of the fractionated radiation therapy of a patient. Each time the patient is setup for the treatment, the Lucite top cover plate of the tungsten powder block-forming container 66 with the lead blades 136 is inserted on the top of the block forming container 50 before the radiation. Tungsten blades instead of lead blades could also be used for this partial beam intensity filtration. Alternatively a simple lead cut with desired thickness placed on tope of the central block forming Styrofoam cut is sufficient for the desired beam's intensity modulation. Both these methods of beam's intensity modulation are simple than beam's partial filtered intensity modulation with much complex and very expensive MLCs.

What is claimed is:

1. A dynamic radiation therapy field shaping system with multiple radiation sources arranged in a circle and combined with a computerized tomotherapy device for image guided all field simultaneous conformal radiation therapy by means of 2, 3, 4 or more radiation sources and beam shaping blocks made in conformity with the shape of the tumor and said conformal blocks are made with the aid of a plurality of block making assembly, one for each of the radiation sources and said radiating beam is shaped in conformity with the shape of the tumor as it is seen per each beam's eye view to treat a tumor through 2, 3, 4 or more fields simultaneously and said conformal dynamic filed shaping is with the aid of simulating conformal light beam seen as coming from each of the radiation sources and passing through Styrofoam that is cut in conformity with the shape of the tumor in a patient who is treated and placed underneath the radiation source to aid to make the said dynamic conformal block and comprising:
   a. multiple radiation sources configured in a circle
   b. a computerized tomography device for imaging
   c. field shaping block configured with Styrofoam cuts that conform with the anatomy of the target tumor,
   d. field shaping block making assembly comprising an upper and lower reservoir for holding fluid material used for field shaping block,
   e. said field shaping blocks made as dynamic instantaneous blocks by dispensing the block forming material from the reservoirs located on a platform below each of the radiation sources.

2. The system of claim 1 wherein the dynamic instantaneous field shaping block making assembly further comprises field shaping polystyrene foam cuts made in conformity with the divergence of the radiation beam for dispensing the block forming melted Cerrobend or tungsten powder from said reservoirs located on a platform below the beam source.

3. The system of claim 2 wherein the field shaping block making assembly further comprises polystyrene foam cuts holding removable thermoplastic trays with etched markers for centered fixing of the polystyrene foam cuts and melted Cerrobend or tungsten powder in conformity with center and convergence of the light and radiation fields of the system.

4. The system of claim 3 wherein the dynamic field shaping block that modulates the beam from each radiation source is made by directly filling the space in between the central and lateral polystyrene foam cuts that is placed on to a block forming tray directly below each radiation source and filling it with tungsten powder or melted Cerrobend that is freely moving or flowing from block making material holding reservoir after removal of the mid polystyrene cut.

5. The system of claim 3 wherein the field shaping block is made as dynamic instantaneous block with melted Cerrobend or with tungsten powder and the patient who is simulated to render radiation therapy is placed on to the treatment table that is surrounded by multiple radiation sources equipped with said filed defining blocks and said radiation sources and radiation defining blocks as arranged in a circle for all field simultaneous radiation therapy.

6. The system of claim 3 wherein the dynamic and instantaneous field shaping block assembly that is placed underneath each of the radiation sources and comprising a dispenser for dispensing the block making material from the lower reservoir to the upper reservoir before a patient's radiation therapy for treatment field shaping and beam's modulation and after said treatment emptying the Styrofoam cuts and returning the field defining material to the lower reservoir and to reuse the same field defining material for next patient's treatment.

7. The system of claims 4 wherein the field shaping block comprises a dynamic on line Cerrobend block made of freely flowing melted Cerrobend with a patient setup on treatment table for immediate radiation therapy.

8. The system of claim 7 wherein the field shaping block making assembly further comprises a heating unit to melt the Cerrobend and to keep it as melted, and dispenser for dispensing of the melted Cerrobend from the lower reservoir to the upper reservoir and for returning the melted Cerrobend to the lower reservoir as a means for dynamic field shaping with melted Cerrobend during the treatment setup of a patient on the treatment table.

9. The system of claim 1 for dynamic instant easily and repeatedly radiation therapy field defining block making with block making material such as with tungsten powder or melted Cerrobend that is automatically filled into Styrofoam cuts for geometrically conformal irregular treatment field shaping with the aid of online kilovolt computerized tomography of the tumor site in a patient and said field encompassing the planning treatment volume seen as per beam's eye view and for attenuating the radiating beam intensity with radiation absorbers inserted into the beam's path and automatic filling and emptying of the field making material from the Styrofoam cuts into attached field shaping material holding reservoirs before and after the radiation therapy and said field shaping system attached directly beneath each of the multiple radiation sources arranged circularly around a treatment table for all field simultaneous radiation therapy.

10. The system of claim 9 wherein the field shaping block comprises a tungsten powder block or a melted Cerrobend block and the radiating beam intensity absorbers consist of three layers of stacked 0.6×15×2 mm sized tungsten or lead blades with cm markers and said radiating beam intensity absorbers as fixed at the top of a 0.5 cm thick thermoplastic tray that forms the upper cover of the upper reservoir.

11. The system of claim 10 wherein the beam intensity absorbers are disposed close to each other and fixed in place with tongue and groove arrangement.

12. The system of claim 11 wherein the beam shaping block has an open field and the beam intensity absorber blades are adjustable by sliding them towards or away from the radiating beam passing through the open field.

13. The system of claim 12 wherein the beam intensity absorbers moved on to the path of the beam passing through the open field shaped by the field shaping block for selective absorption of a desired percentage of radiation reaching the tumor and the planning treatment volume encompassing the tumor by selectively adjusting the number of blades and its thickness to render intensity modulated radiation therapy.

14. An image guided and intensity modulated all field simultaneous radiation therapy system combined with a kilovoltage computerized tomography system and 2, 3, 4 or more radiation sources arranged in a circle and with a plurality of dynamic block making assembly, one for each of the radiation sources and said radiating beam is shaped in conformity with the shape of the tumor as it is seen per each beam's eye view to treat a tumor through 2, 3, 4 or more fields simultaneously and said system for each radiation source's beam shaping block making consists of reservoirs filled with block making material comprising tungsten powder or melted Cerrobend and Styrofoam cuts to aid to make the blocks and said block making system is placed on a tray directly below the radiation sources and the space formed in between the Styrofoam cuts is automatically filled in and emptied from said block making materials and its such repeated use and said radiating beam's intensity is modulated with thin layers of stacked tungsten or lead blades.

15. The system of claim 14 wherein the radiating beam intensity is modulated with beam intensity modulating absorbers that are inserted into the path of the beam or moved away from the path of the beam.

* * * * *